(12) United States Patent
Arnell et al.

(10) Patent No.: US 6,713,024 B1
(45) Date of Patent: Mar. 30, 2004

(54) ODOR DISPENSING DEVICE AND ODOR DISPENSING CARTRIDGE

(75) Inventors: John Arnell, Bishops Stortford (GB); Christos Pavlos Bakopoulos, Cardiff (GB); Ahmet Ennis Baydar, West Roxbury, MA (US); Philippe Blondeau, Paris (FR)

(73) Assignee: Aroma Technology Limited, Bishops Stortford (GB)

(*) Notice: Subject to any disclaimer, the term of this patent is extended or adjusted under 35 U.S.C. 154(b) by 0 days.

(21) Appl. No.: 09/763,984

(22) PCT Filed: Aug. 24, 1999

(86) PCT No.: PCT/EP99/06193

§ 371 (c)(1),
(2), (4) Date: Apr. 24, 2001

(87) PCT Pub. No.: WO00/12143

PCT Pub. Date: Mar. 9, 2000

(30) Foreign Application Priority Data

Aug. 28, 1998 (EP) .............................................. 98116305

(51) Int. Cl.$^7$ ................................................ A62B 7/08
(52) U.S. Cl. ............................... 422/124; 422/4; 422/5; 422/120; 422/125; 422/306; 239/57; 239/60; 392/386; 392/390
(58) Field of Search .............................. 422/124, 4, 5, 422/120, 125, 305, 306; 239/57, 60; 392/386, 390

(56) References Cited

U.S. PATENT DOCUMENTS 4,603,030 A    7/1986  McCarthy
4,629,604 A  * 12/1986  Spector .................... 422/124
4,952,024 A    8/1990  Gale
5,565,148 A   10/1996  Pendergrass, Jr.
6,024,783 A  *  2/2000  Budman .................... 96/222

FOREIGN PATENT DOCUMENTS

EP           0295129       12/1988
EP           0546214        6/1993
WO           WO 9702076     1/1997

\* cited by examiner

Primary Examiner—Krisanne Thornton
(74) Attorney, Agent, or Firm—Birch, Stewart, Kolasch & Birch, LLP

(57) ABSTRACT

The invention relates to an odor dispensing device comprising a housing and a disc shaped cartridge (3, 32) adapted to move around its rotation axis and having a plurality of discrete radially arranged compartments (5, 33), each compartment (5, 33) containing an odorant or an odorant carrier (6, 58), said housing containing means for positioning the cartridge (3, 32), means for producing an airstream to a pre-selected compartment (5, 33) in response to a signal emanating from a computer control module, a microprocessor, an optical system or a timing mechanism and means for temporarily subjecting the odor carrier (6, 58) within the compartment (5, 33) to the airstream so that an odor is discharged from the cartridge (3, 32), and entrained in the airstream, wherein the cartridge (3, 32) has a basic body (4, 34) with bottom (4f, 51) and compartments (5, 33) separated by walls, which compartments (5) of the cartridge (3) can be tightly closed and opened by covers (11) working in axial direction of the cartridge (3) and against the flow of the airstream.

34 Claims, 19 Drawing Sheets

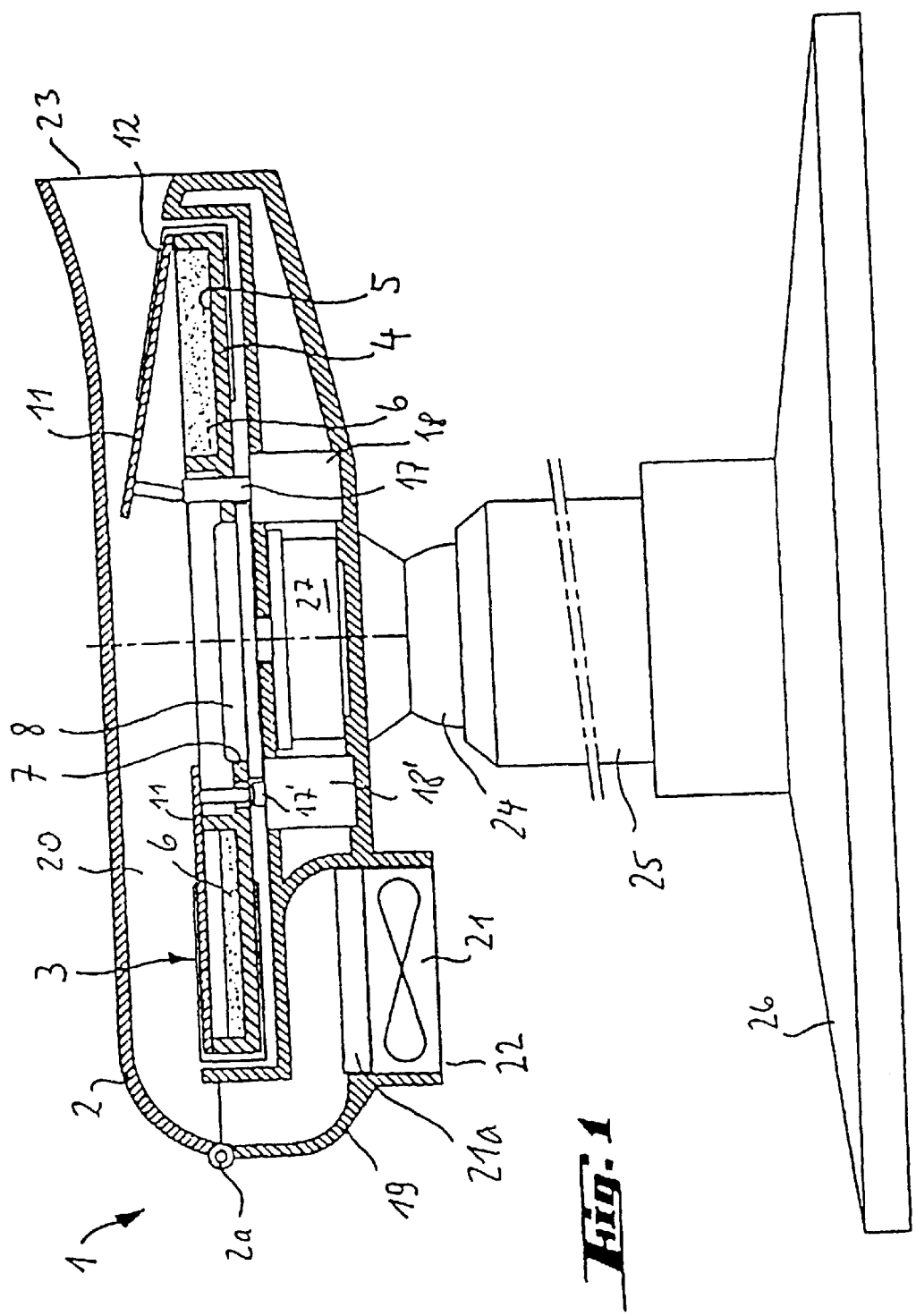

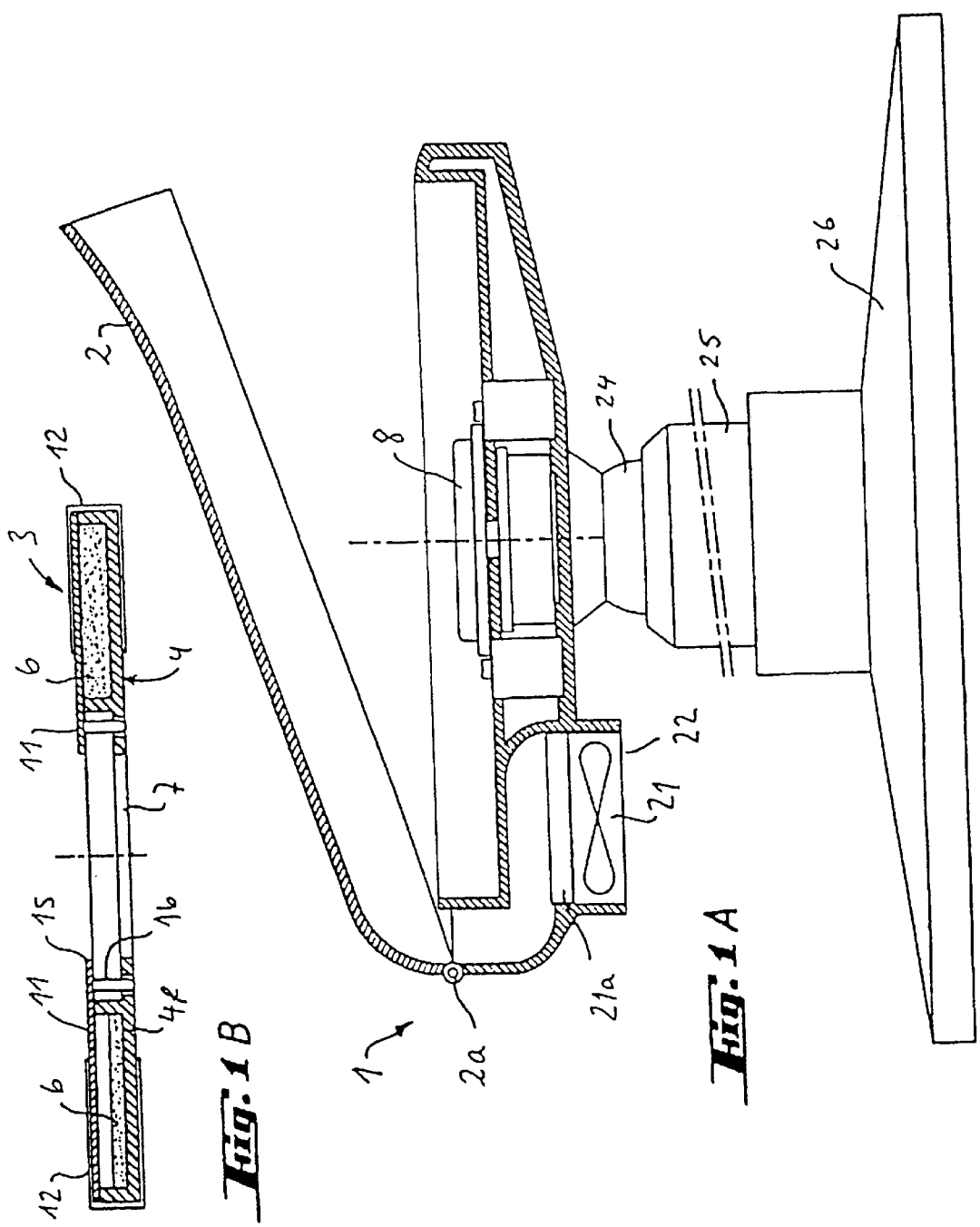

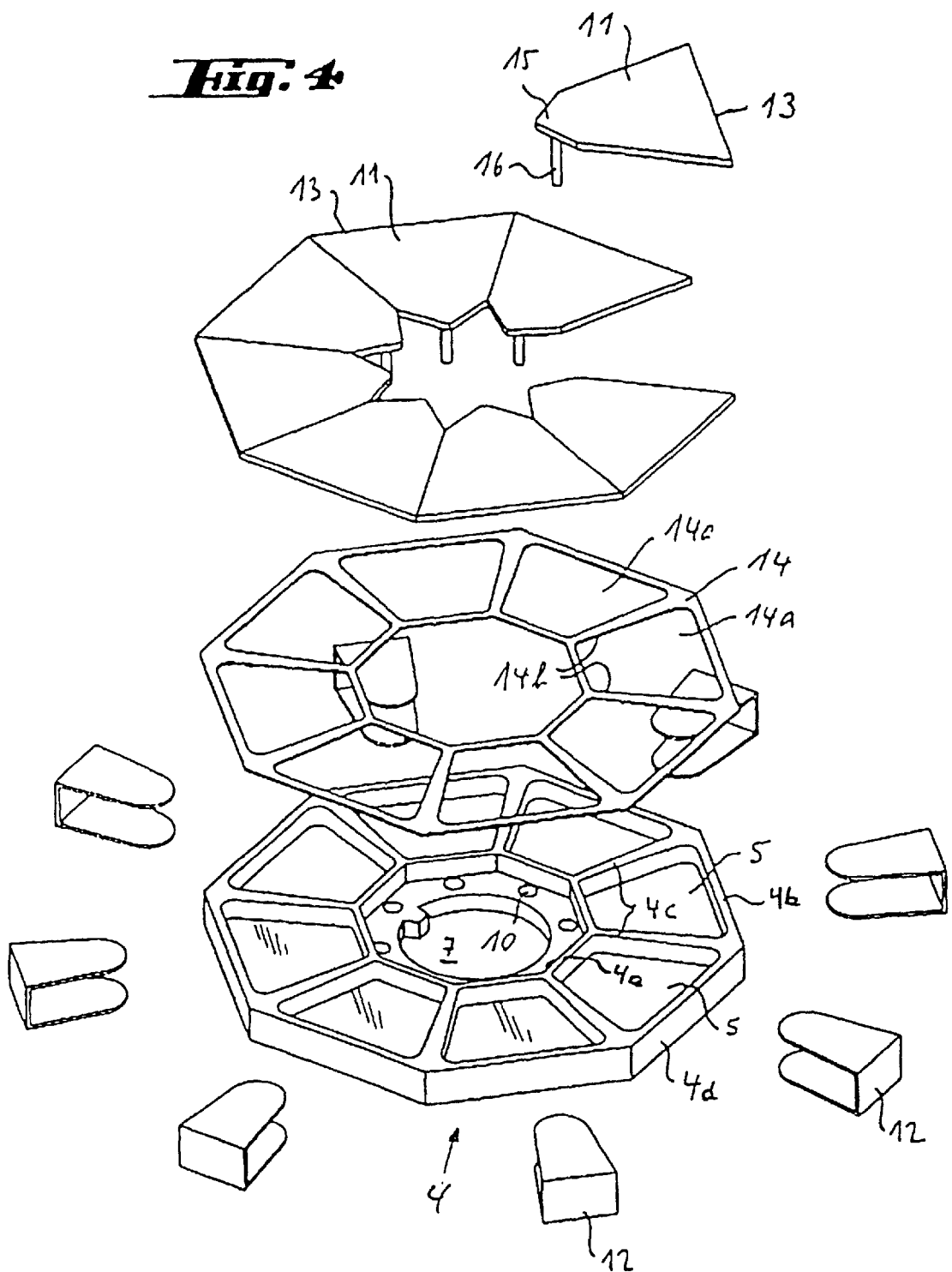

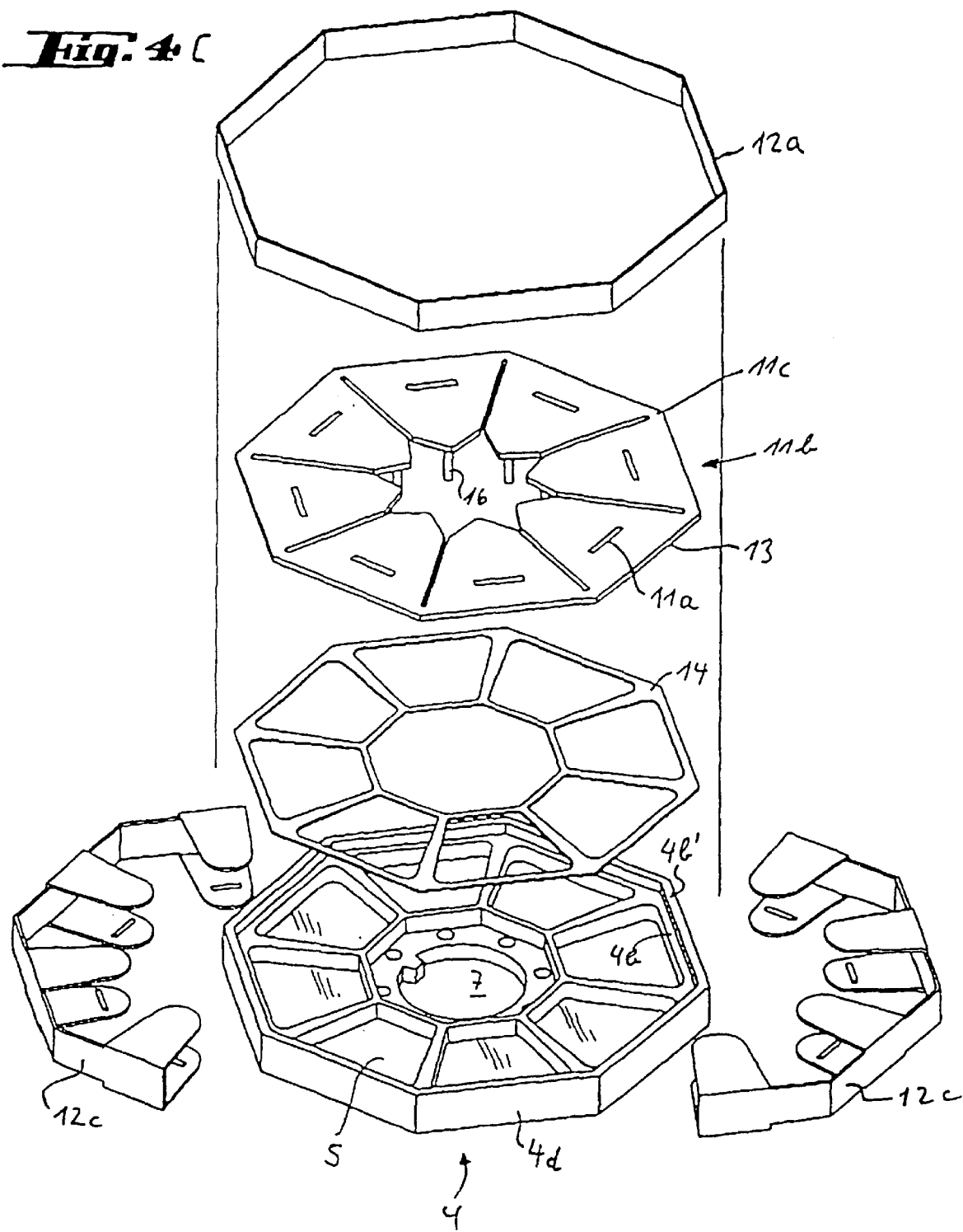

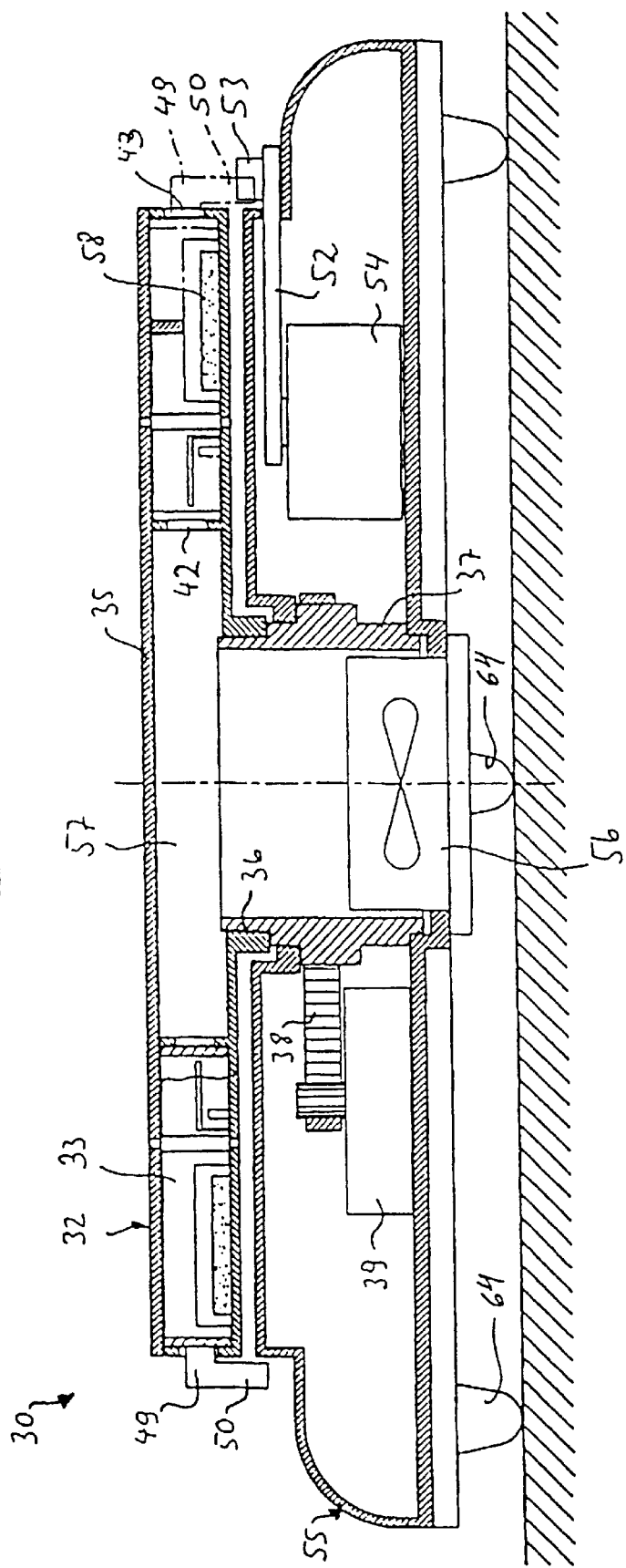

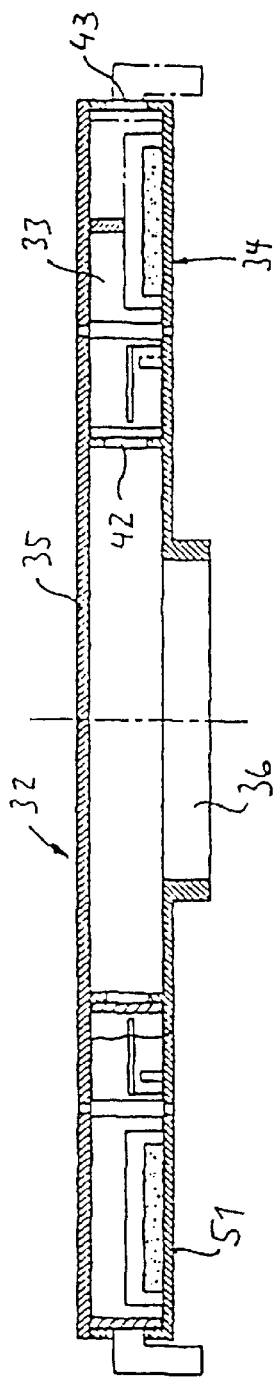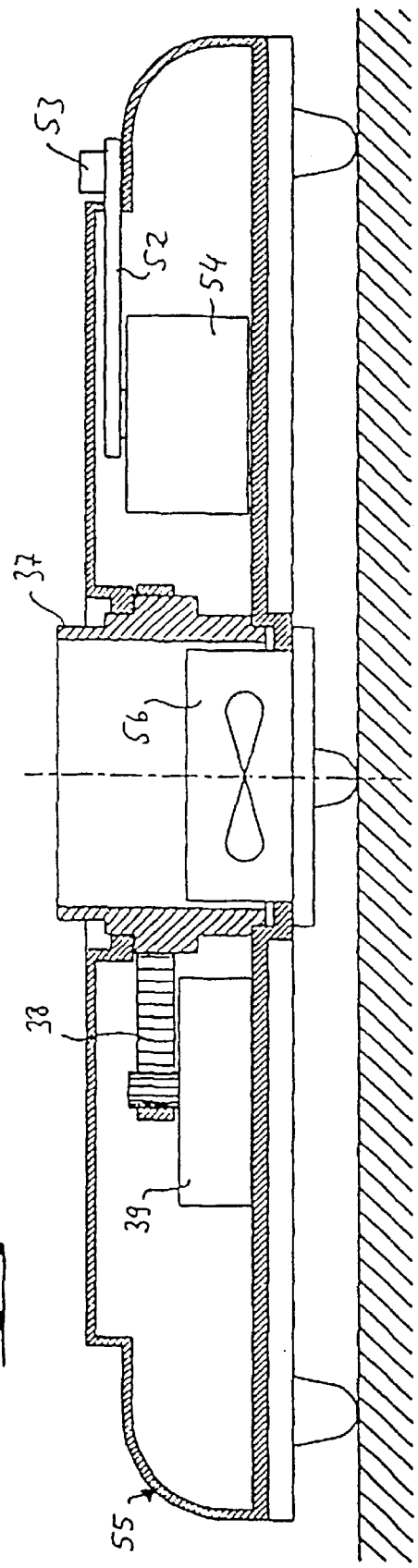

ODOR DISPENSING DEVICE AND ODOR DISPENSING CARTRIDGE

This application is the national phase under 35 U.S.C. § 371 of PCT International Application No. PCT/EP99/06193 which has an International filing date of Aug. 24, 1999, which designated the United States of America.

FIELD OF THE INVENTION

The present invention relates to an odor dispensing device comprising a housing and a disc shaped dispensing cartridge adapted to move around its rotation axis and having a plurality of discrete radically arranged compartments, each compartment containing an odorant on an odorant carrier, said housing containing means for positioning the cartridge, means for producing an airstream to a pre-selected compartment in response to a signal emanating from a computer control module, a microprocessor, an optical system or a timing mechanism and means for temporarily subjecting the odor carrier within the compartment to the airstream so that an odor is discharged from the cartridge and entrained in the airstream, and to an odor dispensing cartridge.

BACKGROUND OF THE INVENTION

Personal computers and microprocessors are now routinely used in all aspects of life and the introduction of multi-media and virtual reality technology is widespread in business, leisure and educational environments. The multimedia industry in particular has made significant technological advances in enhancing the video graphics and audio playback quality of their products. Virtual reality is specifically intended to simulate the real world as closely as possible allowing a participant to take a view in three dimensional space. Virtual reality technology now allows production of sound within the virtual world and to a more limited extent, tactile capability.

In order to enhance further the experience created by multi-media or virtual reality, it will be necessary to develop the technology to include the capability to use the senses of smell and taste as well.

It is an object of the present invention to provide an odor dispensing device and an odor dispensing cartridge for dispensing odors in conjunction with multi-media or virtual reality technology to enhance the real life effect, especially in conjunction with computer games, videos or television and/or music.

It is a further object of the present invention to provide an odor dispensing device and an odor dispensing cartridge to dispense odors into an interior atmosphere, especially to refresh the atmosphere surrounding people in living rooms, motor cars and in public transport.

It is therefore a further object of the present invention to provide an odor dispensing cartridge and a device for its use to dispense selectively a plurality of odors or fragrances.

Numerous devices have been previously proposed for releasing fragrances into an interior atmosphere in order to stimulate the olfactory sense. Such devices are often referred to generically as "air freshener" devices.

Typically such air freshener devices release fragrance by passive evaporation or by employing an active release mechanism such as a pressurized aerosol mechanism which can by manually or automatically operated.

It is known that the intensity of a released fragrance decreases with time elapsing from the instant of fragrance emission and therefore repeated release of fragrance can be necessary to maintain a desired fragrance intensity.

Accordingly, it is another object of the present invention to provide a device for dispensing interactively an odor into an interior atmosphere.

It is also suggested that "fragrance fatigue" can occur whereby a persons olfactory organ becomes "saturated" with a particular smell or fragrance and thus the individual becomes insensitive to the presence of the particular fragrance.

It is a still further object of the present invention to provide, in general an odor dispensing device and an odor dispensing cartridge to dispense selectively a plurality of odors or fragrances as desired for supporting sales activities, e.g. in perfumeries, and/or only for pleasure of a person.

A device for delivering odoriferous substances intended for dispersal in the air or air mixtures, in particular individual odors, is already disclosed in WO 97/02076.

The proposed device, the so-called scent compact diskette, comprises a flat disc shaped cartridge through which pass a number of separate channels substantially parallel to the top face and bottom face and which are directed radially. The channels are formed by an upper diskette half, a lower diskette half and lateral channel divisions in the form of two-sided, elongated dividing ribs in the diskette. They thus form small, radially arranged flat tunnels. The odoriferous substances, which may be partly the same or all different, are introduced into the channels or the odoriferous substances are introduced in gastight reservoirs which are placed in the channels which each reservoir release the individual odoriferous substance only when it is to be dispersed.

Each channel has one inlet aperture and one outlet aperture and allows unrestricted passage of a gas (air) stream introduced via the inlet aperture. The inlet and outlet apertures of the channels are gastight sealed until the odoriferous substance of an individual channel is released by rupture of the appropriate seals of the channel and/or by rupture of the appropriate reservoir if the substance is introduced in the channels in afore mentioned reservoirs.

This device allows the diffusion of a scent coincident with the showing of films or videos, and/or in combination with playing music, thus offering a complete audio-visual olfactory experience.

The production of the diskette is very laborious and, hence, very expensive because a lot of manufacturing steps are involved and, further, some steps must be performed very precisely, especially those of the gastight sealings and/or the introduction of the reservoirs into the channels. Each odoriferous substance can only be used once because after rupture of the apertures and/or the reservoir by the first use of one specific channel this might allow unrestricted and uncontrolled, respectively, passage of a gas (air) stream, i.e. uncontrolled flow of the odoriferous substance being introduced in that channel.

BRIEF SUMMARY OF THE INVENTION

According to the present invention, there is provided an odor dispensing device and an odor dispensing cartridge which both are simple and, hence, can be easily producted and therefore are inexpensive.

According to the invention the odor dispensing device comprises an odor dispensing device comprising a housing and a disc shaped cartridge adapted to move around its rotation axis and having a plurality of discrete radically arranged compartments, each compartment containing an odorant on an odorant carrier, said housing containing means for positioning the cartridge, means for producing an airstream to a pre-selected compartment in response to a signal emanating from a computer control module, a microprocessor, an optical system or a timing mechanism and means for temporarily subjecting the odor carrier within the compartment to the airstream so that an odor is discharged from the cartridge and entrained in the airstream wherein the cartridge has a basic body with bottom and compartments separated by walls, (a) which compartments can be tightly closed and opened by covers working in axial direction of the cartridge and against the flow of the airstream whereby in the closure position the covers are pressed on opening edges of the walls, or (b) which each compartment has a closable inlet aperture and an interrelated closable outlet aperture for passing of a part the airstream, thereby in the opening position in both cases (a) and (b) picking up the particular scent of the odorant on the odorant carrier which scented airstream is then discharged into the surrounding air of the housing.

According to the invention the odor dispensing cartridge comprises a basic body with bottom and a plurality of discrete radically arranged compartments separated by walls, each compartment containing an odorant on an odorant carrier, and (a) can be tightly closed and opened by covers working in axial direction of the cartridge whereby in the closure position the covers are pressed on opening edges of the walls, or (b) which each compartment has a closable inlet aperture and an interrelated closable outlet aperture.

According to a first aspect of the invention, the signals emanate from a computer control module and in response to a signal the cartridge is oriented and operated such that the airstream is led to a pre-selected compartment containing the required odorant on the odorant carrier picking up the particular scent and discharging it.

According to a second aspect of the invention the signals emanate from a timing mechanism, or alternativel, from an optical system.

Preferably the device is provided with two selectively operable actuating means which control entry of the airstream into each compartment. In an especially preferred embodiment, the selectively operable actuating means are pin operated responsive to signals emanating from the computer control module.

The invention will hereafter be explained by way of examples with reference to the accompanying diagrammatic drawings in which also further details are shown which drawings are presented solely for non-limiting purpose of further illustrating the invention.

SUMMARY OF THE DRAWINGS

FIG. 1 shows a cross-section through a first exemplary variant of an odor dispensing device with an inserted odor dispensing cartridge, FIG. 1A shows the device according to FIG. 1 without the odor dispensing cartridge but with partly opened hood, FIG. 1B shows the odors dispensing cartridge according to FIG. 1, FIG. 4 shows an exploded view of the odor dispensing cartridge according to FIG. 3, FIG. 4C shows an exploded view of a further variant similar to that of FIG. 4, FIG. 5 shows a cross-section through a second exemplary variant of an odor dispensing device with a second exemplary variant of an odor dispensing cartridge, FIG. 5A shows the odor dispensing device of FIG. 5 without the odor dispensing cartridge, FIG. 5B shows the odor dispensing cartridge according to FIG. 5.

DETAILED DESCRIPTION OF THE INVENTION

Figure 2:
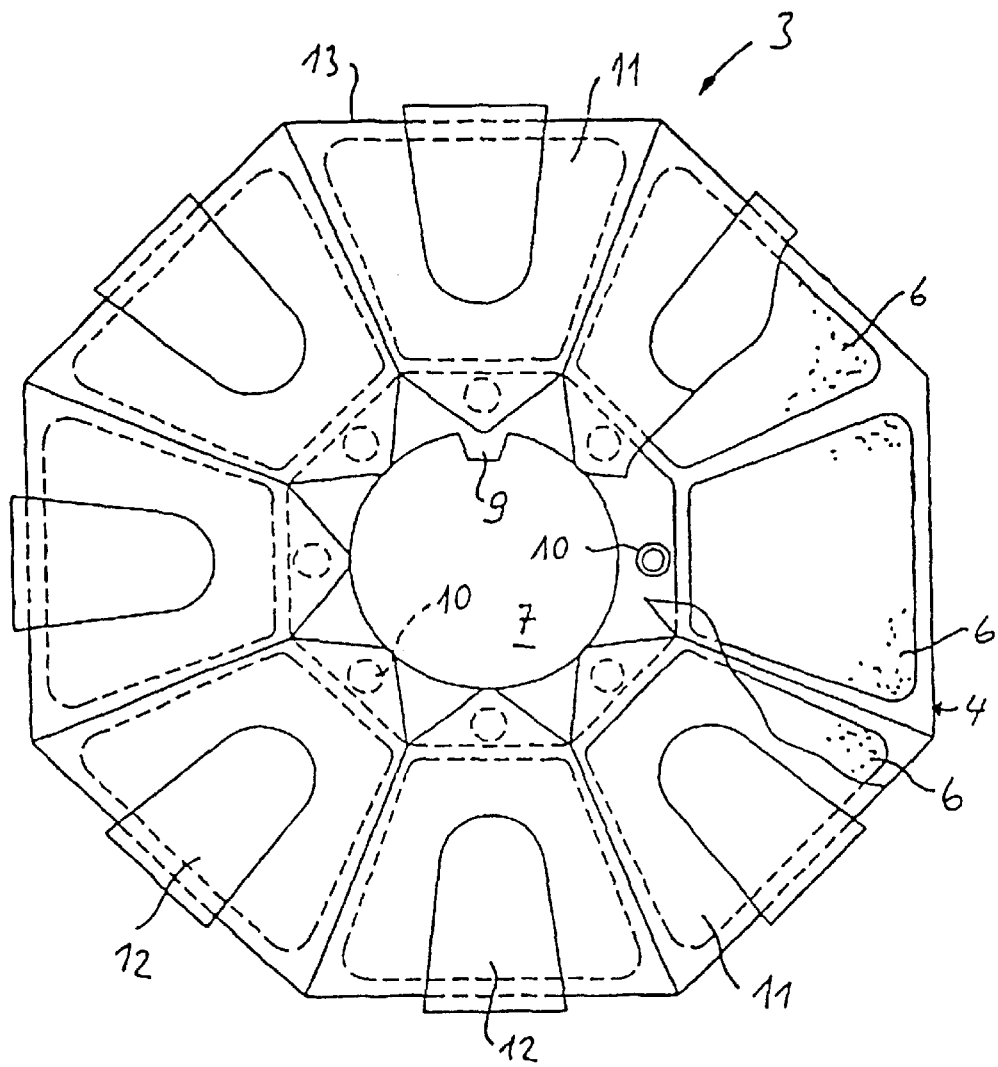
FIG. 2 shows a top view of an odor dispensing cartridge according to FIG. 1 with covers partially broken away.

By way of example, FIG. 1 shows an odor dispensing device according to the invention denoted by 1. FIG. 1A shows the odor dispensing device 1 without the odor dispensing cartridge 3 and FIG. 1B separately shows the odor dispensing cartridge 3. The odor dispensing device 1 substantially consists of a housing 19 and an odor dispensing cartridge 3 which can be positioned therein. The odor dispensing cartridge 3, whose individual components can be seen in FIGS. 2–4, for example, has a basic body 4 with compartments 5, of which there are eight for example in this case, for receiving odorants on an odorant carrier 6. The compartments 5 which have opening edges 4a, 4b, 4c build by the basic body 4 and are open towards the top are trapezoidal in shape, for example, in this case. Other shapes of the compartments 5 are, of course, conceivable. An acceptance opening 7 with a carrier and positioning device 9 for a drive shaft 8 of the housing 19 is provided in the central region of the odor dispensing cartridge 3. Through-openings 10 for control elements described in greater detail below can also be seen in the basic body 4.

Figure 3:
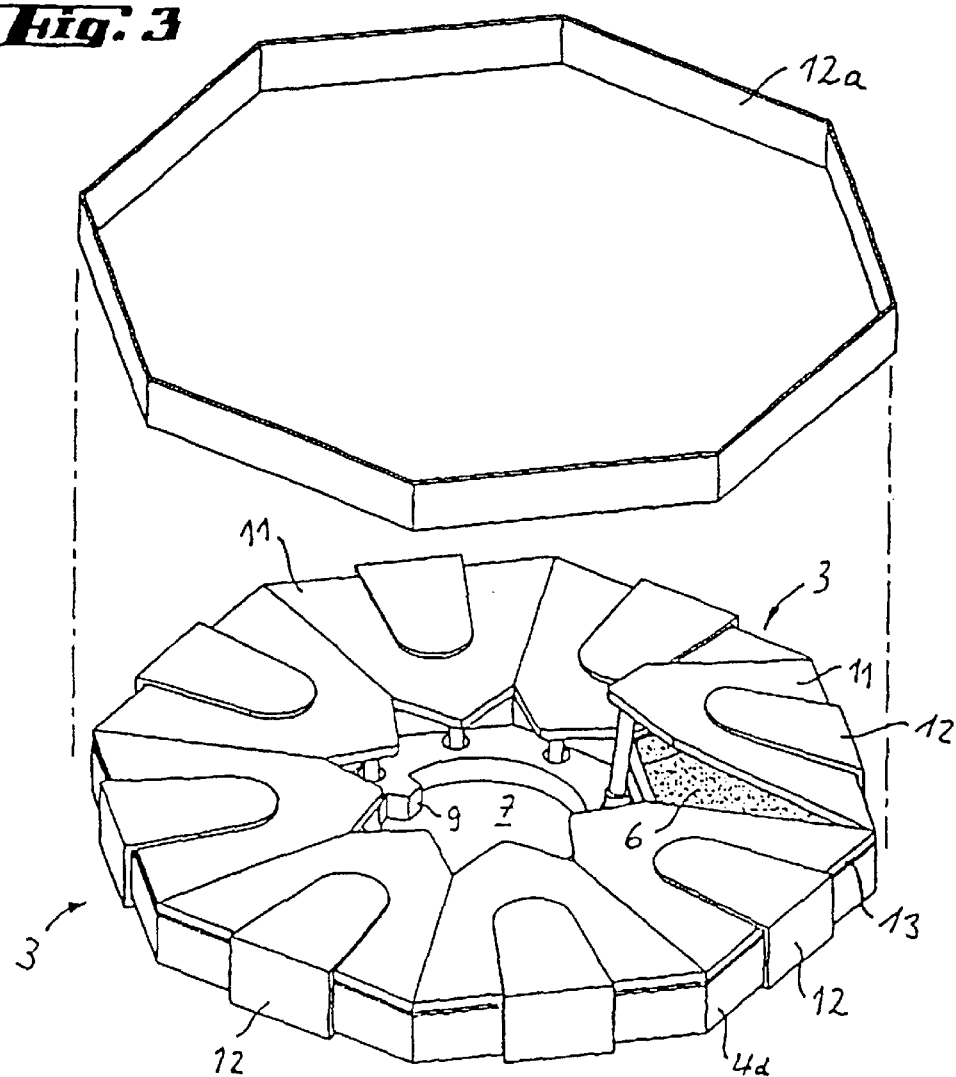
FIG. 3 shows a perspective view of an odor dispensing cartridge according to FIG. 3, wherein a compartment is opened.
Figure 3A:
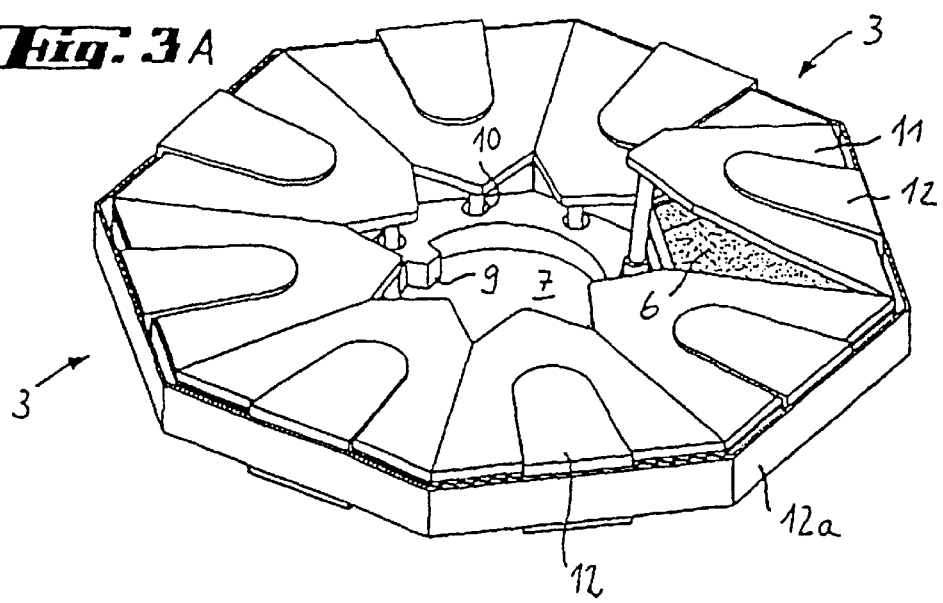
FIG. 3A shows the odor dispensing cartridge with mounted securing band.

A cover 11 matched corresponding to the shape of the compartments is allocated to each compartment 5. The covers 11 are each connected to the basic body 4 via a spring clip 12 arranged in radially external manner and may be arranged in such a way that the radially external edges 13 of the covers 11 form hinges, so to speak, about which the covers 11 may be swivelled into their particular position. The covers 11 are thereby pre-stressed, i.e. pressed tightly onto the opening edges 4a, 4b, 4c in the closed position. The spring clips 12 are secured by a security band 12a as shown in FIGS. 3 and 3A. The elastic arms of the spring clip 12 and the appropriate cover 11 and the bottom of the compartment 5 can be provided with tongues and grooves 4e, 11a, 12b as specifically can be seen in FIGS. 4A and 4B. The spring clips 12 can be additionally secured 4e, 11a, 12b therewith and, further, their correct position is stabilized.

Figure 4A:
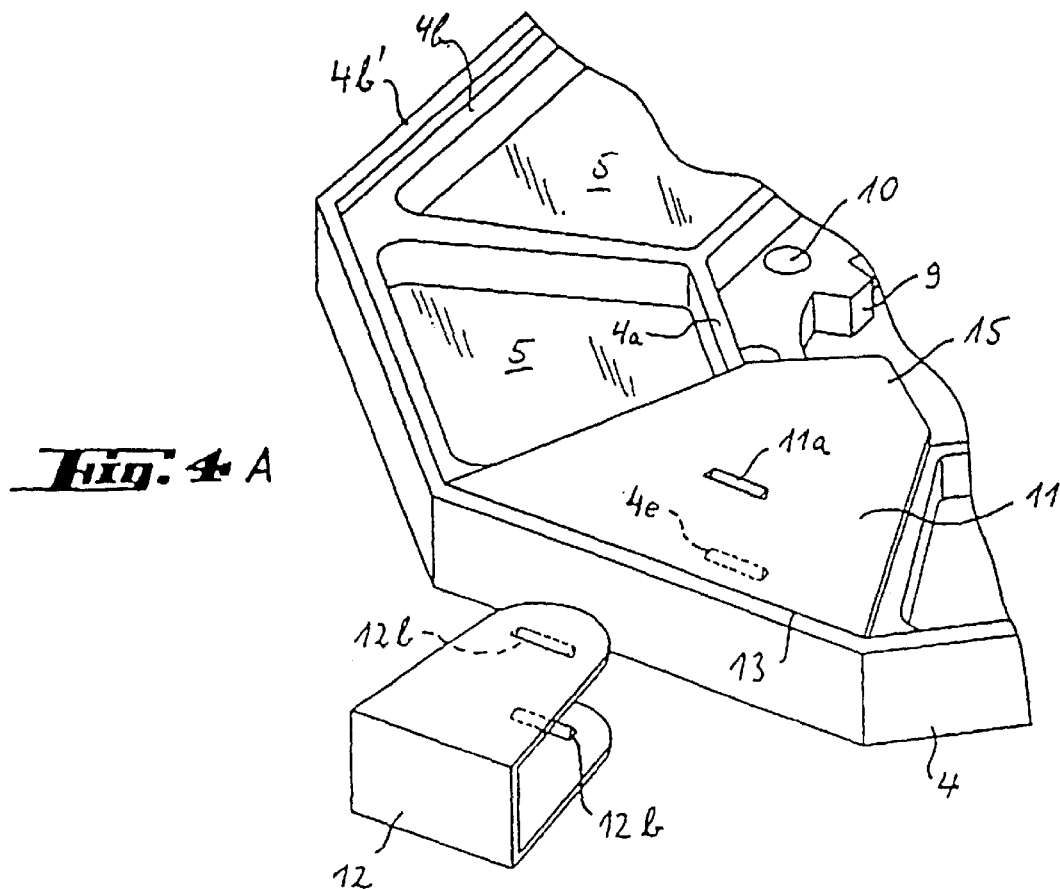
FIG. 4A shows a detailed view of a variant of the odor dispensing cartridge according to FIG. 4.
Figure 4B:
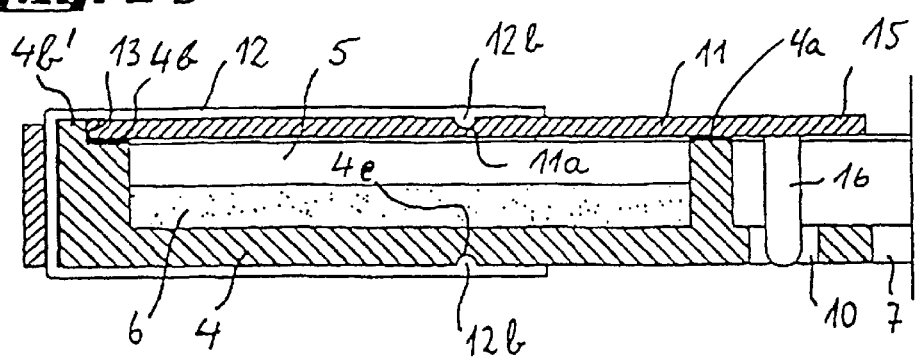
FIG. 4B shows a cross-section of a closed compartment according to FIG. 4A.

For a better guiding of the covers 11 the basic body 4 can contain rims 4b' at their external opening edges 4b as can further be seen on FIGS. 4A and 4B. These rims 4b' have a tickness of about the size as the tickness of the covers 11 and build a ring in which the covers 11, especially the just hereafter described one single piece 11b are/is placed.

FIG. 4C shows a further variant of the covers 11. All covers 11 here are manufactured in one production step, e.g. stamped out of one sheet of plastic or moulded, yielding one single piece 11b whereby the covers 11 are held jointly together by linking bars 11c. By this way as well the manufacture of the covers 11 as also their mounting is made easier.

Figure 4D:
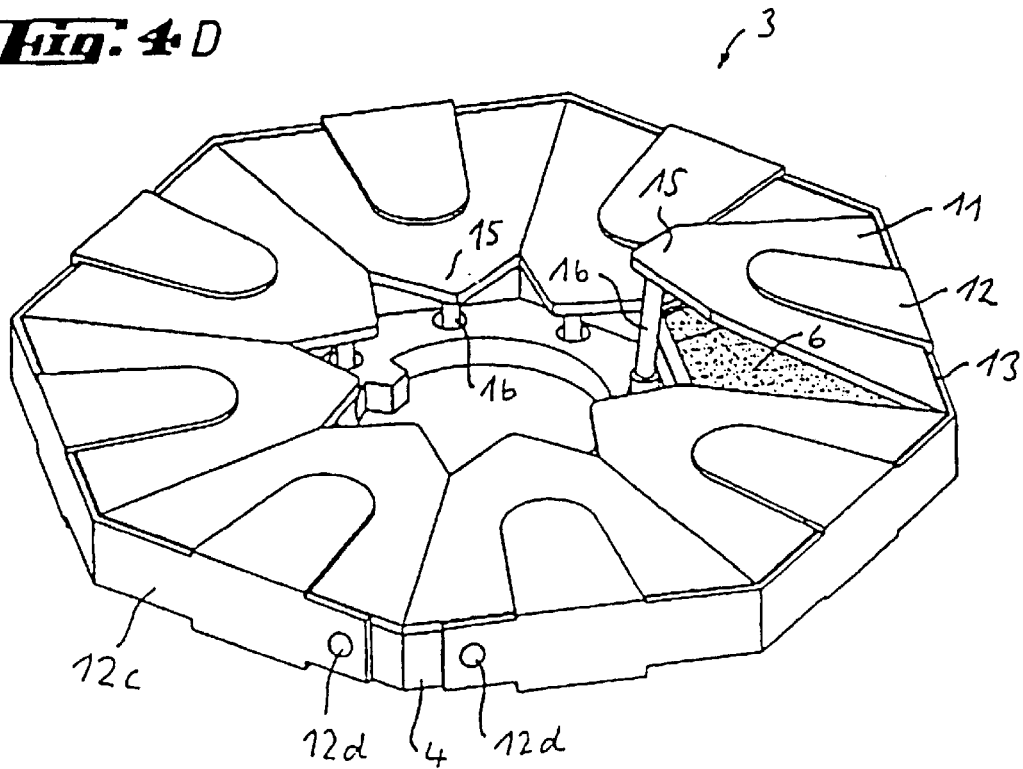
FIG. 4D shows a perspective view of an odor dispensing cartridge with mounted securing band.
Figure 4E:
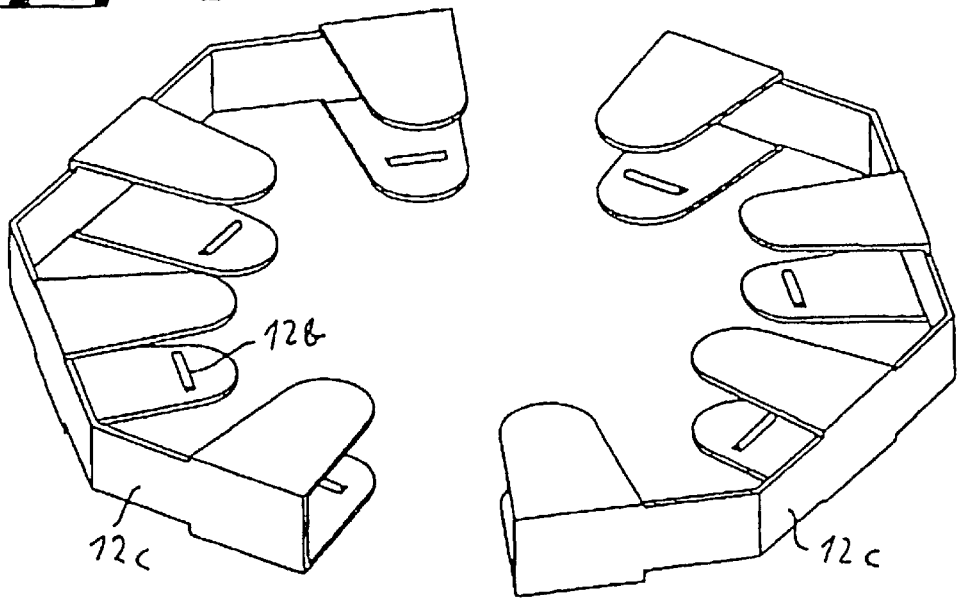
FIG. 4E shows a further variant of a securing band.

For further simplification of the mounting according to FIGS. 4C to 4E the spring clips 12 can be linked together by one or more bands 12c made of the same material as the spring clips 12 which bands 12c can be fixed at the basic body 4 by sealing(s) 12d so that further securing of the spring clips 12 is not necessary as specifically is shown in FIG. 4D. The opening edges 4a, 4b, 4c of the compartments 5 are provided with a flat seal 14 which ensures a reliable sealing of the compartments 5 when the covers 11 are closed. The flat seal 14 contains openings 14a thereby building bounderies which coincidence with the open edges 4a, 4b, 4c of the covers 11. Projections 15 of the covers 11 project over the opening edges 4a of the compartments 5. Pegs 16 may be fixed at the projections 15 which point downwards and pass through corresponding holes 10 of the basic body 4 in the closed condition of the covers 11.

By means of an actuation element 17 which acts directly on the projection 15 or via the peg 16 the projection 15 may be pushed up via an actuation device 18 whereby the cover 11 is swivelled over the hinge against the pre-stress of the spring clip 12 and the odor-emitting substance of the odorant carrier 6 may thus be exposed to the air stream inside a flow duct 20 build by the hood 2.

The air flow can be produced by any mechanical means, especially it is produced by means of a fan 21 whose suction opening 22 is substantially diametrically opposite to the exhaust opening 23 (FIG. 1) which fan 21 may further be associated with a heating element and/or an ionizer 21a. The swivelled-up cover 11 acts as a flow barrier and provides a good turbulence and/or a uniform mixing and distribution of the odor molecules in the air stream without contaminating the parts of the device and/or cartridge 3 because the odor molecules by this way are always surrounded with fresh air, i.e. building an odor cloud in fresh air. This has the advantages that the following dispensed odor is not contaminated with the previous one. As shown in FIG. 1, two actuation elements 17,17' may optionally be provided along with actuation devices 18,18'. With this configuration it becomes possible to dispense two different odors separately without turning the odor dispensing cartridge 3 into another position for this purpose or to dispense a mixture of the corresponding odors.

As can be seen in FIG. 1, the housing 19 may be set on a base surface by means of a ball joint 24, a telescopic stand 25 and a foot 26. The direction of emission of the "fragrance cloud" may be set in different directions by the above-mentioned means. The movable hood 2 is pivoted at the housing 19.

To operate the odor dispensing device 1, first of all an odor dispensing cartridge 3 which separately is shown in FIG. 1B is placed onto the drive shaft 8 of the odor dispensing device 1 which is separately shown in FIG. 1A and fixed in reproducible manner in the direction of rotation via the carrier and positioning device 9. The odor dispensing device 1 is ready for use after the hood 2 (not shown in greater detail) which partially defines the flow duct 20 has been closed. The odor dispensing cartridge 3 may be rotated via the drive shaft 8 and the drive device 27 in such a way that the compartment 5 with the desired fragrance is positioned for opening by the actuation element 17 (FIGS. 1, 3).

All actions of the actuation element(s) 17,17' and the drive device 27 are synchronized via corresponding signal lines, which are not shown, and are connected to an external control device (not shown).

FIG. 5 shows a further variant of an embodiment of an odor dispensing device, namely an odor dispensing device 30 with an odor dispensing cartridge 32 placed outside the housing 55. FIG. 5A shows the odor dispensing device 30 without the odor dispensing cartridge 32 and FIG. 5B separately shows the odor dispensing cartridge 32. As can be seen from the subsequent drawings, the odor dispensing cartridge 32 consists of a basic body 34, for instance having eight compartments 33. The compartments 33 are covered and closed, respectively, by a cover plate 35 which spans the entire basic body 34. According to FIG. 8 a rotary carrier 36 having a fixing acceptance opening 36b with a groove 36a which may cooperate with a correspondingly formed drive shaft 37 of the odor dispensing device 30 is provided in the central region.

For its part the drive shaft 37 is connected, for example via a toothed belt 38, to a drive device 39 and can be rotated in the defined manner corresponding to the compartment spacing.

As shown in FIGS. 6 to 12, at the radially vertical inner boundary wall 40 and outer boundary wall 41 each compartment 33 is provided with an inlet aperture 42 and an outlet aperture 43 which may be closed and/or opened via a rotary slide arrangement 44. The rotary slide 44 has an inner closure element 45 and an outer closure element 46 which are allocated to the apertures 42, 43, are substantially diametrically opposed and are connected to a pivot 48 by means of a bar 47. With respect to the rotational movement of the rotary slide 44 specified by the pivot 48, the closure elements 45, 46 and the boundary walls 40, 41 of the compartments 33 have a mutually matched geometry in such a way that the apertures 42, 43 are tightly closed in the closed position of the rotary slide 44.

A lug 49 projecting radially outwards through the outlet aperture outer 43 is provided on the closure element 46 as rotary slide adjustment element. At the bottom this lug 49 is angled to form a tongue 50 and may extend beyond the lower boundary plane 51 of the odor dispensing cartridge 32. The lug 49 serves to limit the rotary movement of the rotary slide 44 since in its end position it may strike the corresponding edges of the outlet aperture 43.

Figure 12:
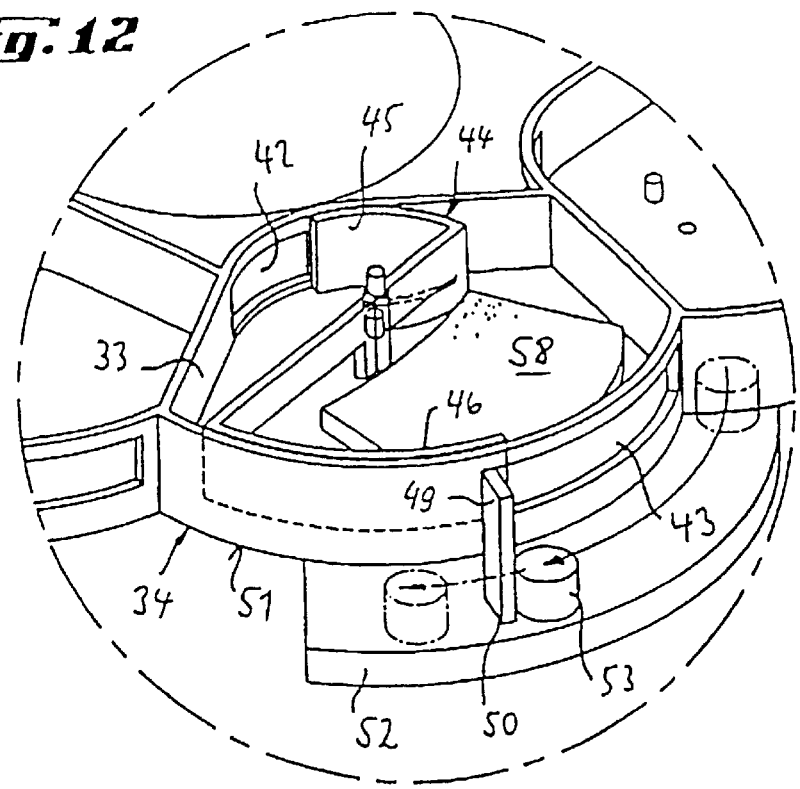
FIG. 12 shows a partial perspective view according to FIG. 6 with opened rotary slide.

As can be seen from FIGS. 5, 6, 11 and 12, the rotary slide 44 is opened via the lug/tongue 49,50 by a control lever 52 on whose radially external end a control projection 53 is provided. With a drive unit (a motor) 54 the control lever 52 is swivel-mounted in the housing 55 of the odor dispensing device 30. The movement path of the control projection 53 is designed in such a way that it substantially coincides with the movement path of the lug 50 and may act thereon (FIG. 6) when a compartment 33 and/or the odor dispensing cartridge 32 has been rotated into the corresponding position. The control projection 53 may be brought from a rest position—in this position the control projection 53 is under the odor dispensing cartridge 32 in a region which does not project into the movement path of the tongues 50 dictated by the rotation of the odor dispensing cartridge 32—into the region of a tongue 50 of a rotary slide 44 and open the latter (FIG. 12). If the compartment 33 is opened an air stream produced by means of a fan 56, but which can be produced by any mechanical means, may enter the central distributor chamber 57 through the hollow drive shaft 37 and thence enter the compartment 33 through the inlet aperture 42, picks up volatilized fragrance molecules from the odor carrier 58 arranged in the compartment 33, and makes its way out into the environment through the outlet aperture 43. The fan 56 may further be associated with a heating element and or an ionizer.

If the rotary slide 44 is formed in such a way that it remains stationary in its open position, after swivelling the control projection 53 back the odor emission angle may be adjusted by means of the drive 54 and/or the odor dispensing cartridge 32 may be continuously rotated for improved spatial distribution (not shown).

Figure 6:
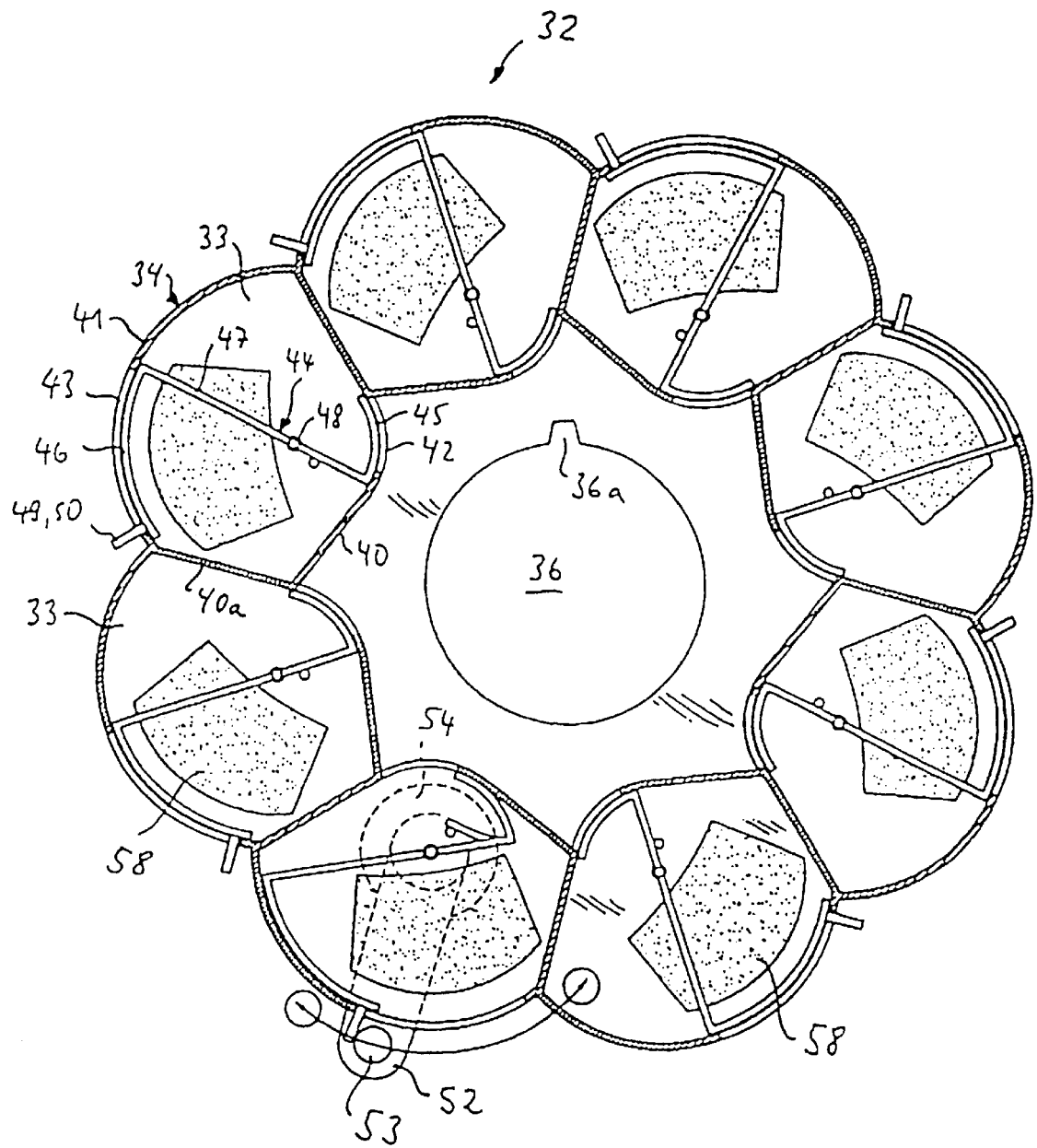
FIG. 6 shows a top view of an odor dispensing cartridge according to FIG. 5B.

In an undifferenciated form FIGS. 6 and 12 illustrate a possible way in which the rotary slide 44 may be closed. In this case the control projection 53 is moved beyond the open position of the rotary slide 44 until the tongue 50 snaps over the latter which tongue 50 in this case, of course, is elastic. When the control projection 53 is guided back, the rotary slide 44 is closed and the control projection 53 moved beyond the closed position so that the tongue 50 snaps over the control projection 53 again.

Figure 8:
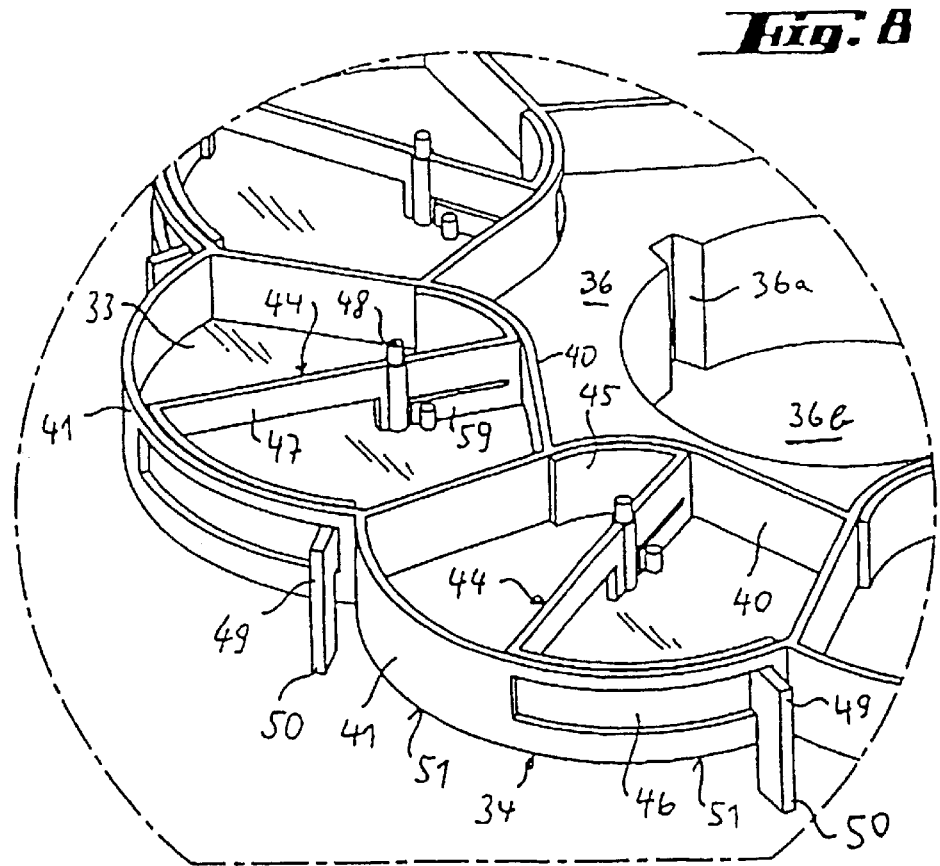
FIG. 8 shows an enlarged detail from FIG. 7.
Figure 9:
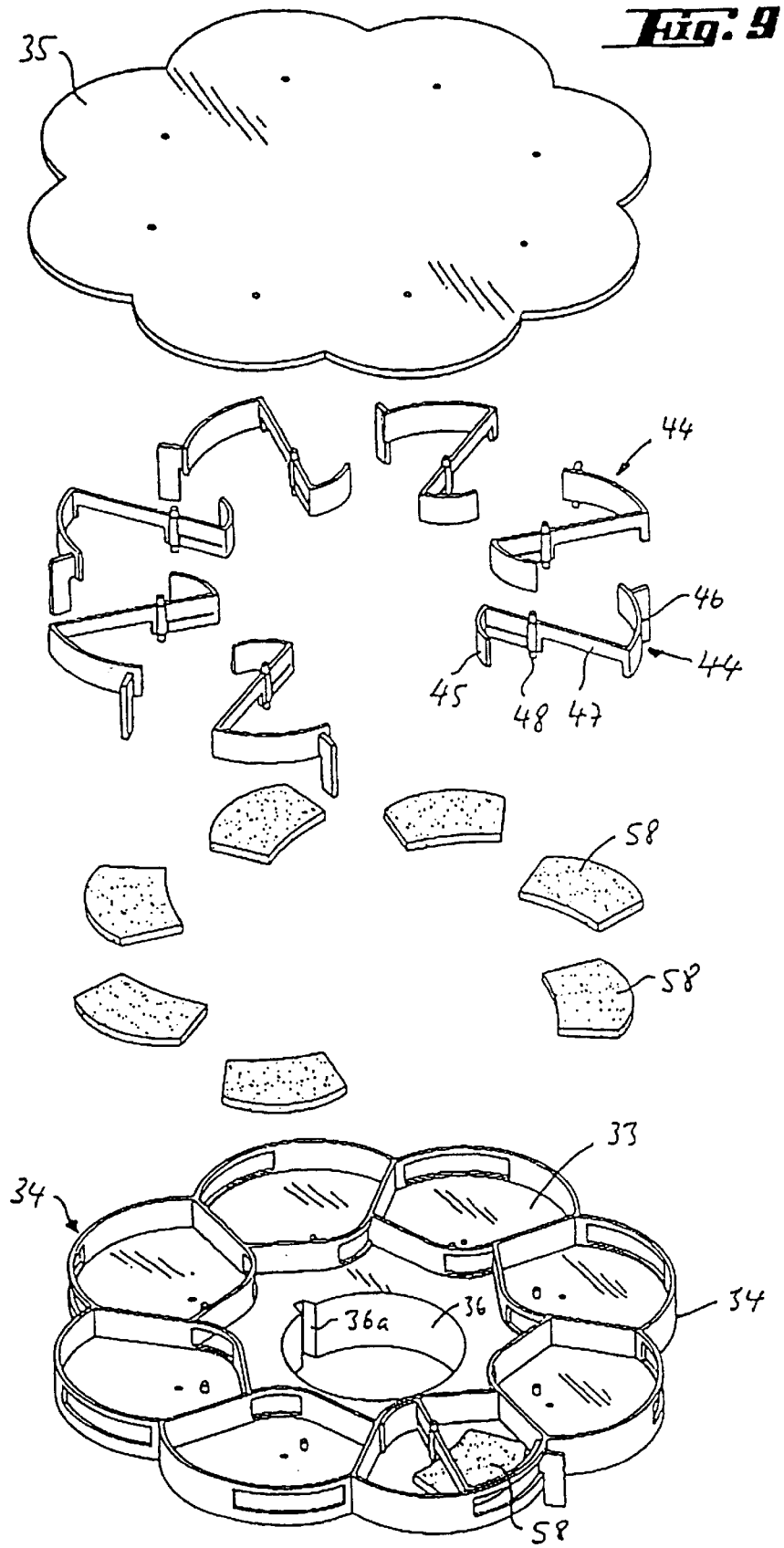
FIG. 9 shows an exploded view of the odor dispensing cartridge according to FIG. 7.
Figure 10:
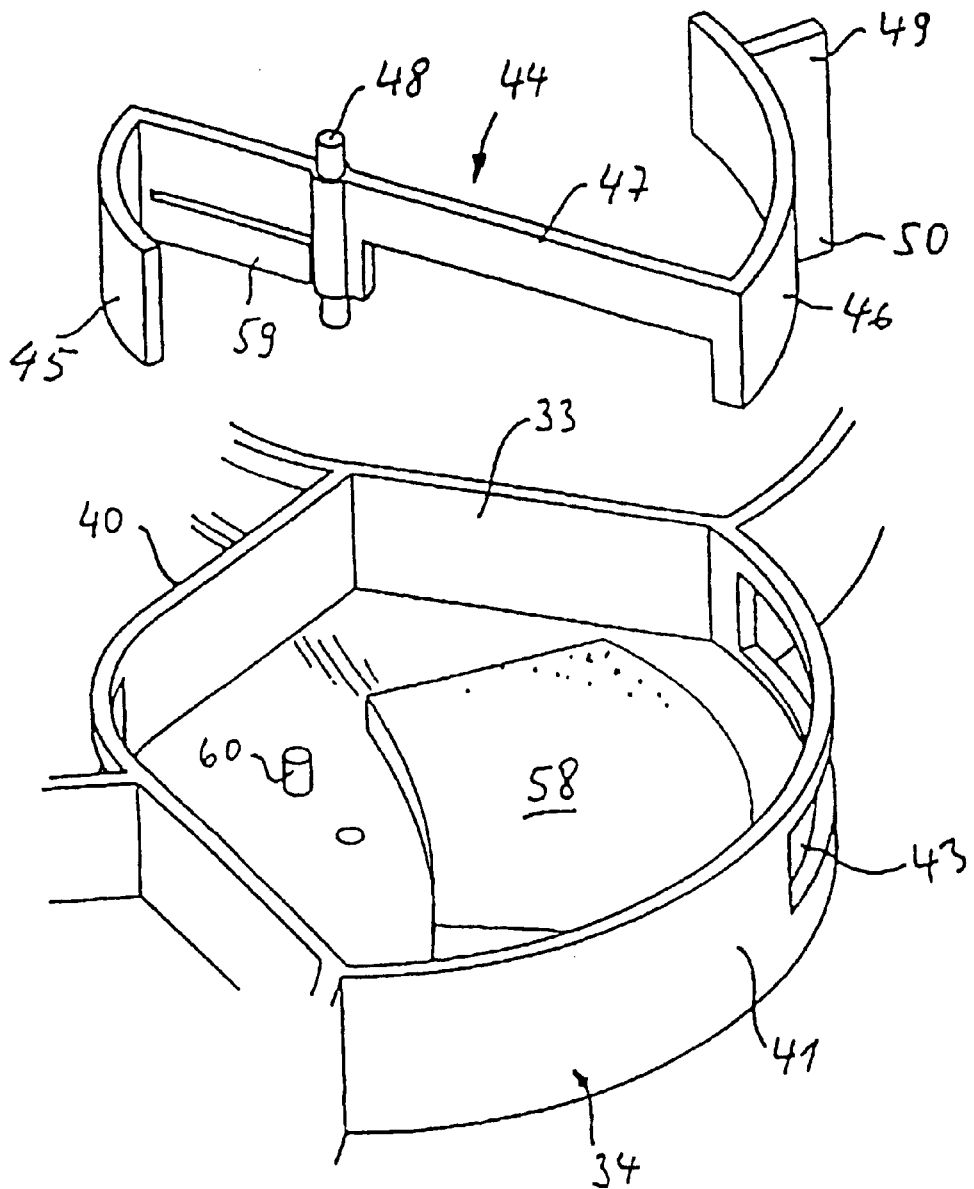
FIG. 10 shows details from FIG. 9.
Figure 11:
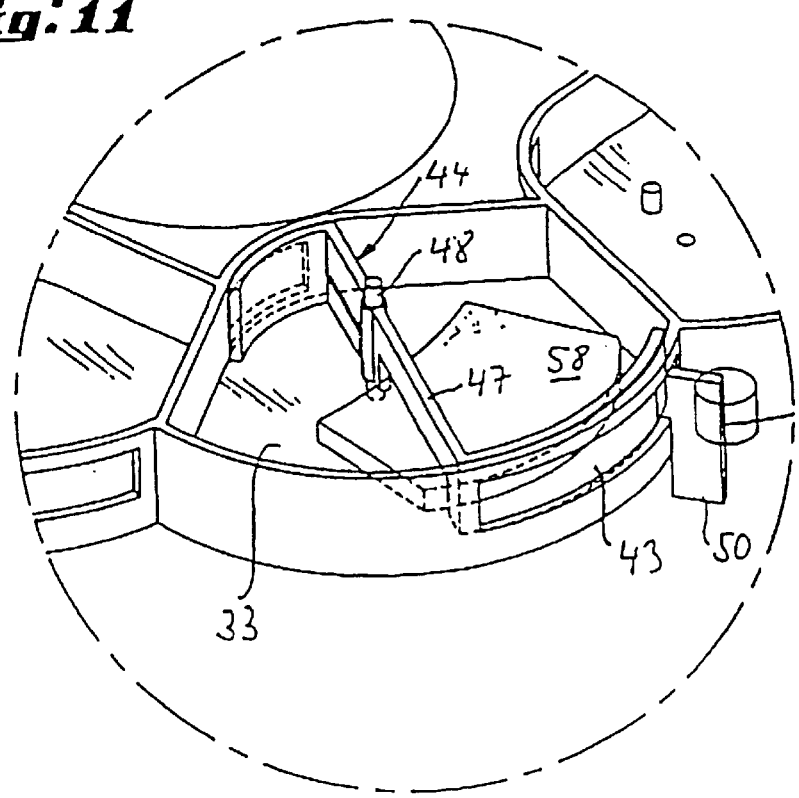
FIG. 11 shows a partial perspective view according to FIG. 6 with closed rotary slide.

In FIGS. 6, 8 and 12, for example, a leaf spring 59 for the automatic closure of the apertures 42, 43 is provided which may be mounted directly onto the rotary slide 44 or moulded together with the rotary slide 44 and is supported at its free side on a projection 60 mounted at the bottom 51 of the compartment 33 and arranged on the base of the basic body 34, respectively. If the control projection 53 recoils back into its rest position the rotary slide 44 is rotated into the closed position by the leaf spring 59.

Figure 6A:
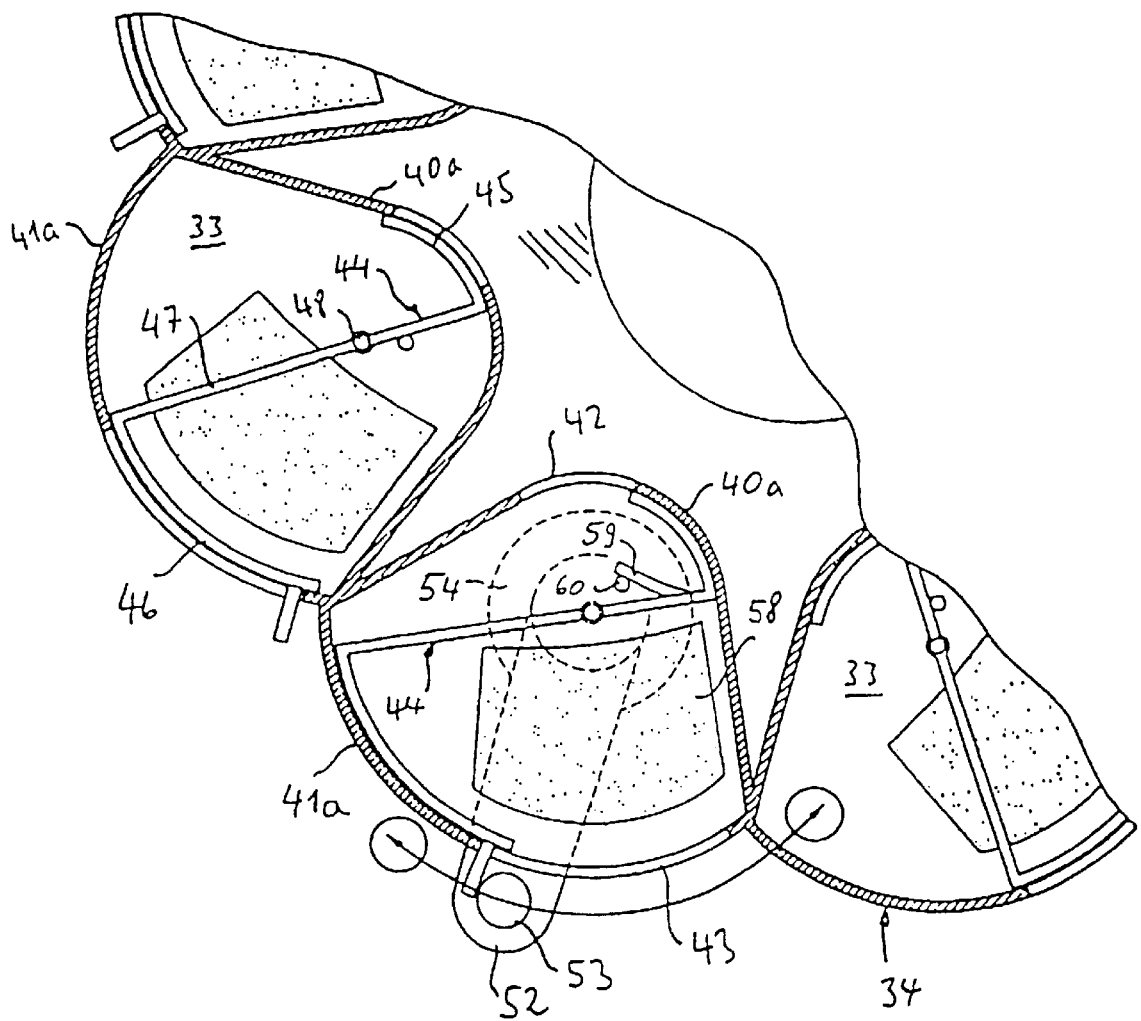
FIG. 6A shows a partly view according to FIG. 6 in a further variant.
Figure 7:
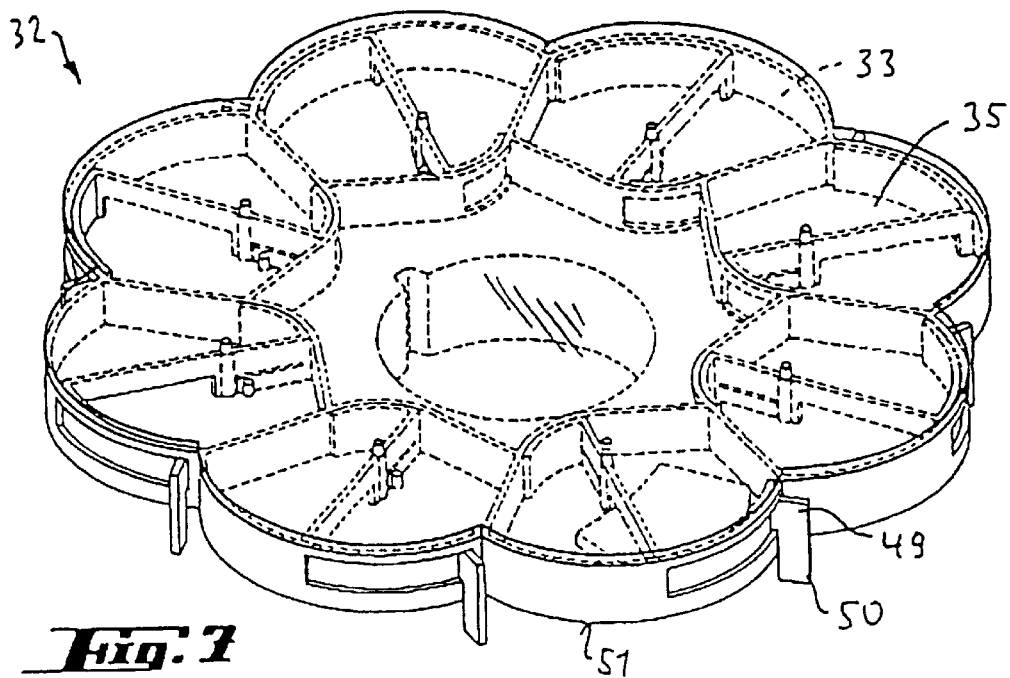
FIG. 7 shows a perspective view of an odor dispensing cartridge according to FIG. 5B.

FIG. 6A shows a further variant of the inner boundry walls 40. In this embodiment the boundary walls 40a are curved over their whole length and have practically the same radius as the inner closure elements 45 of the rotary slides 44.

Figure 13:
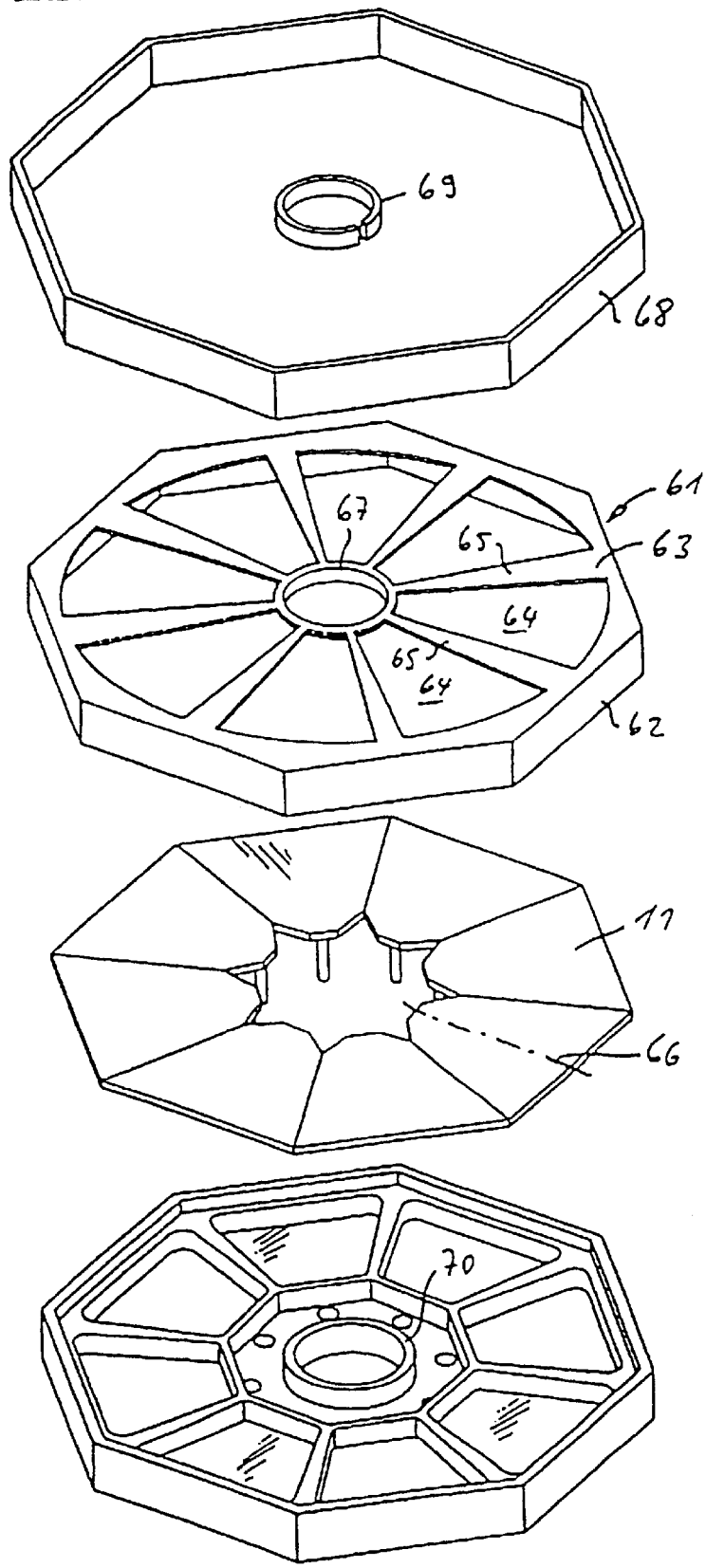
FIG. 13 shows an exploded view of an odor dispensing cartridge similar to FIG. 2 with a further variant of covering the compartments.
Figure 14:
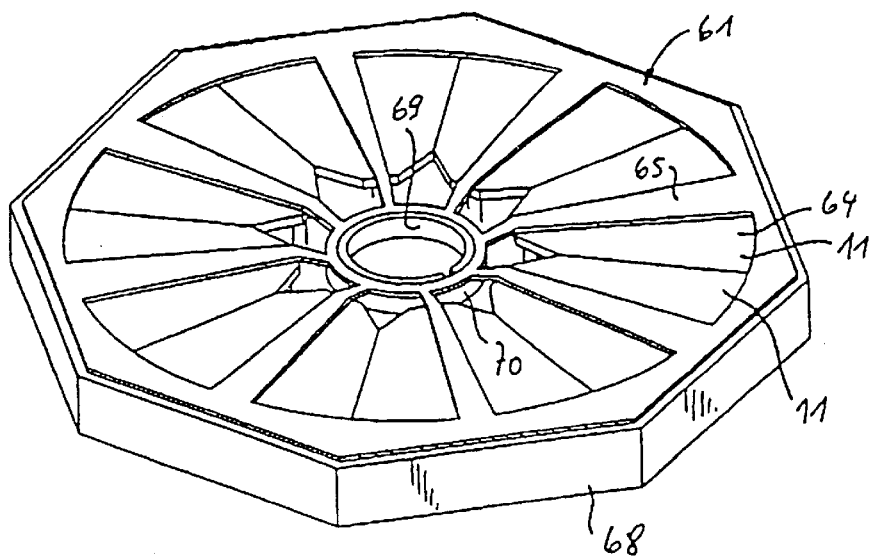
FIG. 14 shows a perspective view of a mounted odor dispensing cartridge according to FIG. 13.
Figure 15:
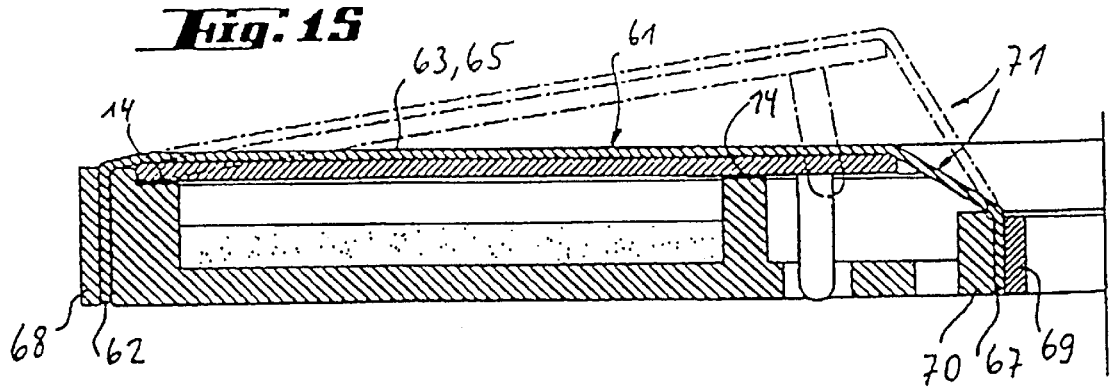
FIG. 15 shows a cross-reaction of a compartment of an odor dispensing cartridge according to FIG. 14

Relative to a cartridge 3 FIGS. 13 to 15 show a further variant for pushing the covers 11 down to the basic body 4 thereby tightly closing the cartridges 5. A piece of rubber 61 consisting of radically arranged rubber bands 65 which are connected with a circular tube-like inner wall 67 at their inner ends and with a circular outer wall 62 at their outer ends, which both walls 67,62 are arranged at right angles to the rubber bands 65, is clamped onto the periphery 4d of the basic body 4. At the acceptance opening 7 the circular tube-like inner wall 67 is secured by a tension ring 69. The rubber bands 65 are running from the middle 66 of the external edges 13 of the covers 11 over the tips of the projections 15 and are under tension thereby pushing the covers 11 downwards. The rubber piece 61 may be further secured at the periphery 4d of the basic body 4 via a clamp ring 68. FIG. 13 shows in an exploded view the parts to be mounted (for a better overview with the exception of the flat seal 14) and FIG. 14 shows the completely mounted configuration. FIG. 15 specifically shows in a cross-section how the rubber piece 61 is positioned and secured and, further, by dashed lines the situation of an opened cartridge 5 is shown whereby the band 65 is expanded in the region 71 near the acceptance opening 7. As soon as the upwards push on the cover 11 is released these are pressed downwards again.

Figure 16:
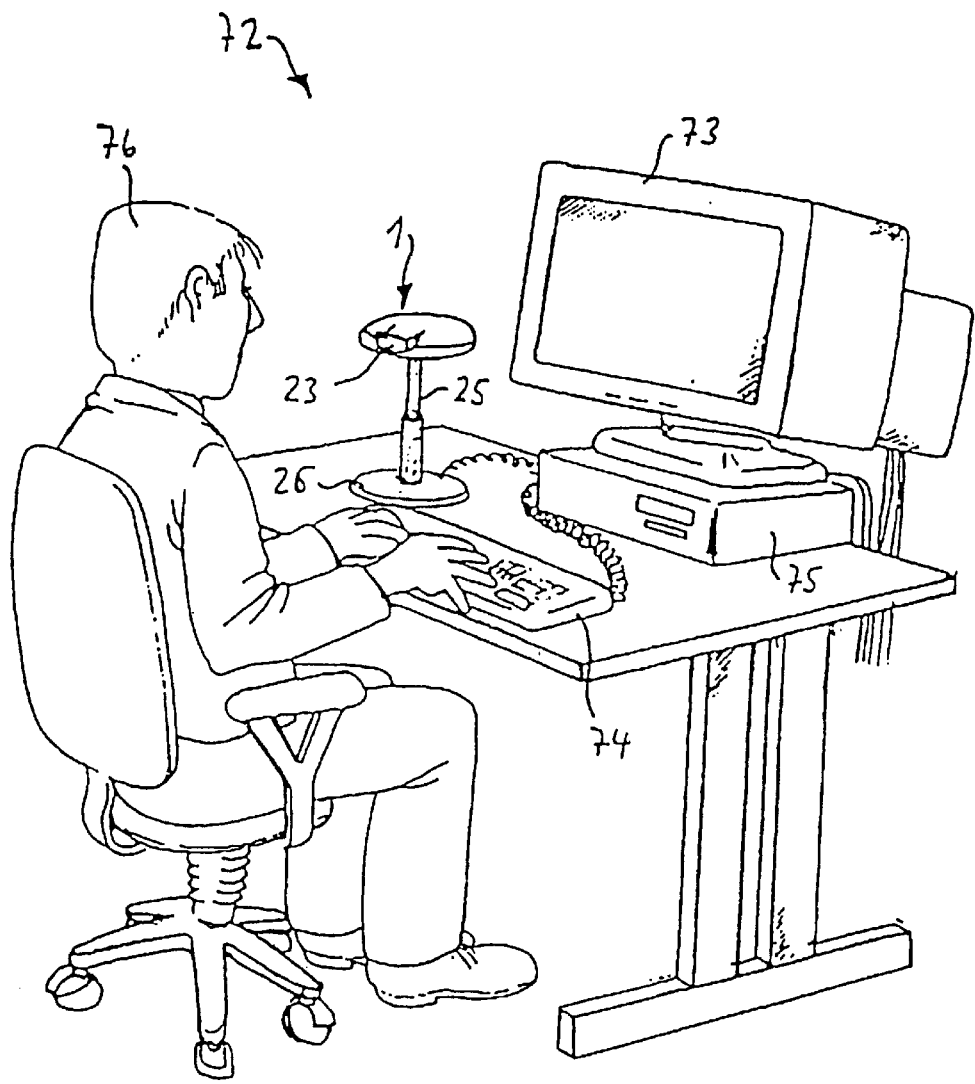
FIG. 16 shows the odor dispensing device of FIG. 1 used in conjunction with a multi media station.

FIG. 16 exemplifies the use of an odor dispensing device according to the present invention, especially the use of a device according to FIG. 1 in combination with a multi media station 73. A video station 7, a non-shown audio station, a keyboard 74 and a computer unit 75 are arranged in such a way that the stimuli of the user's sense-organs nose, eyes and ears are simultaneously optimised.

A device according to FIG. 6 can preferably be used as air freshener whereby the atmosphere of a room, e.g. a cabin of a motor car, can be perfumed with a specific odor according to the preference of the driver or whereby the specific odor can be changed after a predetermined time as programmed by the user to avoid fatigue of the person(s) staying in the room/cabin.

The use of the odor dispensing device 1,30 and the odor dispensing cartridge 3,32, respectively, as air freshener device is also in particular suitable to overcome the well known odor fatigue mentioned at the beginning, whereby the odor is conveniently changed after 2 to 4 hours; this change can be effected by an optical system or can be time triggered.

Especially a device according to FIG. 6 may be equipped in addition with a power source and all actuation and operation means, so building a stand alone unit. Such a stand alone unit might specifically be useful in perfumeries to offer different perfumes to a customer, especially in such preselected quantities that the nose of the customer after having smelled some perfumes can still differenciate further between different perfumes and is not becoming insensible as it otherwise would usually be after smelling three or four perfumes.

All parts of the cartridge 3,32 and practically all parts of the device 1,30, respectively, with the exception of electronic and driving means, may be made of plastic.

The odor carrier 6,58 is prefabricated, preferably in tablet form, and preinstalled in a disposable compartment 5,33. As carrier 6,58 a porous substrate material may be suitable which then may be impregnated with an odorant, e.g. with a perfume oil, by e.g. spraying or dipping and then is inserted in the appropriate compartment 5,33. Each odor dispensing cartridge 3,32 contains a selection of odors that are specific to the desired use and its content and the display associated with it.

The number of individual scents is usually smaller in case of the use of the device 1,30 as air freshener, e.g. 3 to 5, and larger, e.g. 6–8, in case of the use in connection with multi media.

The perfume is usually and conveniently a mixture of any natural and/or synthetic odor and can thus be any fragrance material suitable for imparting the desired odor. Any direction is possible, e.g. fruity, flowery, lavender, vanilla, pine, agrestic or any combination thereof.

Any absorbent/porous material which is inert and does not affect the character of the odor material over time can be used. This carrier material may be natural or synthetic. Suitable porous substrates are organic materials, e.g. especially cellulose, plastics, polyethylene (PE), preferably high density PE with a porous size of about 1–500µ, more preferably of about 20–50 µ, most preferably of about 40µ, and any kind of inorganic materials, e.g. plaster, clay, zeolithes, alumina or ceramics. The substrate can also be in the form of gels. These may be manufactured on the base of carboxy methyl cellulose, carrageenan, polyurethane mousse, stearate, gellan gum, polymeric substrates like agar-agar, or any other gelling agents, e.g. silica or Tween 20 (polysorbate). The preferred high density PE is POREX®. A wide range of grades thereof is available, the most preferred being POREX® X 4903.

In addition, for optimum dispension of the odorant on the odorant carrier 6,58 system, another material can be added to the odor substance. This is a diluent or co-solvent for the perfume. The materials co-act with the perfume to raise or lower the volatility of the perfumes thereby allowing to adjust and control the lifetime. Representative diluents include alcohols, glycols, mineral oils.

Concerning the concentration of the odor material a level starting from pure oil, i.e. from 100%, down to about 20%, diluted in most types of solvents used in the perfumery industry, can be used. Thus, e.g. dipropylene glycol, hexylene glycol, DOWANOL DPM (diporpylene glycol dimethyl ether) or dipropylene glycol mono methyl ether, Carbitol (diethylene glycol mono ethyl ether), paraffinic solvents or ethylphtalate are possible solvents.

The weight ratio of perfume to substrate depends on the substrate material and should be in the range of about 0,05 to about 1,5. Thus, e.g. the level of perfumes in different substrates is advantageously as follows: porous materials: about 5–60%, preferably about 25% by weight; gels used for impregnating the carriers 6,58: about 1–20%, preferably about 10% by weight. The gellified perfumes may contain up to ca. 96% perfume material.

The carriers 6,58 may be in the form of exchangable discs (tablets) depending on the concept of the odor dispensing device 1,30 used but may have a diameter of about 1–30 mm, preferably of about 15–20 mm, the thickness depend also on the concept, but may be preferably 1–10 mm.

What is claimed is:

1. An odor dispensing device comprising a housing and a disc shaped cartridge adapted to move around its rotation axis and having a plurality of discrete radically arranged compartments, each compartment containing an odorant on an odorant carrier, said housing containing means for positioning the cartridge, means for producing an airstream to a pre-selected compartment in response to a signal emanating from a computer control module, a microprocessor, an optical system or a timing mechanism and means for temporarily subjecting the odor carrier within the compartment to the airstream so that an odor is discharged from the cartridge and entrained in the airstream, wherein the cartridge (3,32) has a basic body (4,34) with bottom (4f,51) and compartments (5,33) separated by walls, (a) which compartments (5) of the cartridge (3) can be tightly closed and opened by covers (11) working in axial direction of the cartridge (3) and against the flow of the airstream whereby in the closure position the covers (11) are pressed on opening edges (4a, 4b, 4c) of the walls, or (b) which each compartment (33) of the cartridge (32) has a closable inlet aperture (42) and an interrelated closable outlet aperture (43) for passing of a part the airstream, thereby in the opening position in both cases (a) and (b) picking up the particular scent of the odorant on the odorant carrier (6,58) which scented airstream is then discharged into the surrounding air of the housing (19,55).

2. The device of claim 1 wherein the cartridge (3,32) contains in its central region an acceptance opening (7,36) for a drive shaft (8,37) with a carrier and positioning device (9,36a) placing the cartridge (3,32) in a predifined or start position on a drive shaft (8,37) of a drive device (27,39) contained in the housing (19,55) which drive device (27,39) is capable of rotating the cartridge (3,32) into a specific predisposed position.

3. The device of claim 1 wherein of the cartridge (3) with basic body (4) having a bottom (4f) and compartments (5) separated by walls is placed in the housing (19) and the covers (11) build projections (15) projecting over the internal opening edges (4a) of the compartments (5) in such a manner that in a predisposed position of the cartridge (3) one or two actuation element(s) (17,17') which is/are guided by though-openings(s) (10) of the central part of the basic body (4) point to the projection(s) (15) which each actuation element (17,17') is movable upwards with the help of actuation device(s) (18,18') thereby lifting the cover(s) (11) and opening the appropriate compartment(s) (5).

4. The device of claim 3 containing only one actuation element (17).

5. The device of claim 1 wherein the opening edges (4a, 4b, 4c) of the compartments (5) are provided with a flat seal (14).

6. The device of claim 5 whereby the flat seal (14) is made of one flat piece of elastic material, especially of a rubber sheet, with stamped out parts which one piece of flat seal (14) coincidences with the outlines of the opening edges (4a, 4b, 4c) of the compartments (5).

7. The device of claim 1 wherein each cover (11) is pushed down to the basic body (4) via a spring clip (12) having a U-form and being arranged in a radially external manner.

8. The device of claim 7 wherein the spring clip (12) is connected by an external edge (13) of the cover (11) forming a hinge about which the spring clip (12) is swivelled into its particular position whereby the cover (11) is pressed tightly onto the opening edges (4a, 4b, 4c) of the compartment (5).

9. The device of claim 7 wherein each spring clip (12) is connected with the appropriate cover (11) and/or the basic body (4) by a tongue and grove system (12b, 11a, 4e).

10. The device of claim 7 wherein at least some of the spring clips (12) are linked together by a band (12c) made of the same material as the spring clips (12).

11. The device of claim 10 wherein the band (12c) is secured by heat sealing(s) (12d).

12. The device of claim 7 wherein the isolated spring clips (12) or the spring clips (12) linked together by a band (12c) are secured by an elastic ribbon (12a) surrounding the periphery (4d) of the basic body (4) or the band(s) (12c).

13. The device of claim 1 wherein the covers (11) of the cartridge (3) are pushed down to the basic body (4) by a rubber piece (61) consisting of radially arranged rubber bands (65) being under tension and running from the middle (66) of the external edges (13) of the covers (11) over the tips of the projections (15) and which are connected with a circular tube-like inner wall (67) at their inner ends and with a circular tube-like outer wall (62) at their outer ends which both walls (62,67) are arranged at right angles to the rubber bands (65) whereby the outer wall (62) is clamped onto the periphery (4d) of the basic body (4) and may be secured via a clamp ring (68) and the inner wall (67) is fastened at the acceptance opening (7) via a tension-ring (69).

14. The device of claim 1 wherein the covers (11) are stamped out of a sheet of plastic or are of moulded plastic.

15. The device of claim 3 whereby the contact of the projection (15) with the actuation element (17,17') is performed by a pin (16) being part of the cover (11) and being arranged at right angles to its side directing towards the compartment (5).

16. The device of claim 15 wherein the cover (11) containing the pin (16) is made of moulded plastic.

17. The device of claim 1 wherein all covers (11) are held jointly together by linking bars (11b).

18. The device of claim 2 wherein the air stream is performed by a fan (21), which may further be associated with a heating element and/or an ionizer (21a), and the air stream is directed over the side of the cartridge (3) with the covers (11) by a hood (2) building a flow duct (20) which hood (2) is movable, especially pivoted at the housing (19), for loading and unloading of the cartridge (3).

19. The device of claim 2 wherein the drive device (27) is mounted on a stand preferably on a telescope stand, (25).

20. The device of claim 19 wherein the drive device (27) is mounted with a ball joint (24) on the telescope stand (25) having a foot (26).

21. The device of claim 1 wherein the cartridge (32) is placed outside the housing (55) on the drive shaft (37) which cartridge (32) consists of a basic body (34) with a bottom (51) and compartments (33) arranged around a central acceptance opening (36) and a coverplate (35) whereby the compartments (33) are separated by walls and each compartment (33) further consists of an inner boundary wall (40) with an inlet aperture (42) and an outer boundry wall (41) with an outlet aperture (43) whereby the boundry walls (40,41) are circular at least in the zone of the apertures (42,43) and which apertures (42,43) can be opened and closed by a rotary slide (44) which is placed inside the compartment (33) and is adapted to move around its pivot (48) which is supported between the coverplate (35 and the bottom (51) of the appropriate compartment (33) and the basic body (34), respectively.

22. The device of claim 21 wherein the rotary slide (44) has a Z or S form constituted by a rigid bar (47), which incorporates the pivot (48) at right angles to its longitudinal axis, and an inner closure element (45) and an outer closure element (46) with a lug (49) near its (46) free end which lug (49) conveys the outlet aperture (43) and has an elongated tongue (50) directed to the bottom of the basic body (34), which both elements (45,46) are elastic and during movement of the rotary slide (44) glide closely along the inner sides of the inner and outer boundary walls (40,41) thereby opening or tigthly closing the inlet and outlet apertures (42,43) which movement is performed with the help of the tongue (50) situated outside of the compartment (33) which tongue (50) is moved parallel to the circular arch of the outer boundry wall (41) by a control projection (53) which is driven over a control lever (52) by a motor (54) installed in the housing (55).

23. The device of claim 22 wherein the radius of the circular part of the inner boundry wall (40) is smaller than the radius of the circular part of the outer boundry wall (41).

24. The device of claim 22 wherein the part of the bar (47) between the pivot (48) and the outer closure element 46 has at least partly a distance to the bottom (51) of the basic body (34) for free movement above the odor carrier (58).

25. The device of claim 22 wherein the part of the bar (47) between the pivot (48) and the inner closure element (45) has an attached leaf spring or includes a leaf spring (59) as an integral part which is under tention by being supported at its free side on a projection (60) mounted at the bottom (51) of the compartment (33) thereby keeping the inner and outer apertures (42,43) in the closed position.

26. The device of claim 1 and 21–25 wherein the drive shaft (37) is driven directly by a motor (39) or with the help of a toothed belt (38) which both (38,39) are installed in the housing (55).

27. The device of claim 1 and 21–26 wherein the housing (55) has distance means (64) at and air entrance perforations in the bottom plate and contains a fan (56), which may further be associated with a heating element and/or an ionizer and the drive shaft (37) is a tube being closed at the opposite end of the distributor chamber (57) and having openings through which air may stream to the distribution chamber (57).

28. The device of claim 1 and 21–26 wherein the housing (55) has distance means (64) at the bottom plate and contains a fan (56) placed in the tube-like driving shaft (37) having open ends, which fan (56) may further be associated with a heating element and/or an ionizer.

29. An odor dispensing cartridge (3,32) comprising a basic body (4,34) with bottom (4f/51) and a plurality of discrete radially arranged compartments (5,33) separated by walls, each compartment (5,33) containing an odorant on an odorant carrier (6,58), wherein (a) the compartments (5) of the cartridge (3) can be tightly closed and opened by covers (11) working in axial direction of the cartridge (3) whereby in the closure position the covers (11) are pressed on opening edges (4a, 4b, 4c), or wherein (b) each compartment (33) of the cartridge (32) contains a closable inlet aperture (42) and an interrelated closable outlet aperture (43).

30. The odor dispensing cartridge (3) of claim 29 wherein of the cartridge (3) with basic body (4) having a bottom (4f) and compartments (5) separated by walls is placed in a housing (19) and the covers (11) build projections (15) projecting over the internal opening edges (4a) of the compartments (5) in such a manner that in a predisposed position of the cartridge (3) one or two actuation element(s) (17,17') which is/are guided by through-opening(s) (10) of the central part of the basic body (4) point to the projection (s) (15) which each actuation element (17,17') is movable upwards with the help of actuation device(s) (18,18') thereby lifting the cover(s) (11) and opening the appropriate compartments(s) (5).

31. The odor dispensing cartridge (3) of claim 29 wherein the opening edges (4a, 4b, 4c) of the compartments (5) are provided with a flat seal (14).

32. The odor dispensing cartridge (32) of claim 29 wherein the cartridge (32) is placed outside a housing (55) on the drive shaft (37) which cartridge (32) consists of a basic body (34) with a bottom (51) and compartments (33) arranged around a central acceptance opening (36) and a coverplate (35) whereby the compartments (33) are separated by walls and each compartment (33) further consists of an inner boundary wall (40) with an inlet aperture (42) and an outer boundry wall (41) with an outlet aperture (43) whereby the boundry walls (40,41) are circular at least in the zone of the apertures (42,43) and which apertures (42,43) can be opened and closed by rotary slide (44) which is placed inside the compartment (33) and is adapted to move around its pivot (48) which is supported between the coverplate (35) and the bottom (51) of the appropriate compartment (33) and the basic body (34), respectively.

33. The odor dispensing device according to claim 1 for use as/in air freshener.

34. The cartridge (3/32) according to claim 33 for use in a motor car.

* * * * *